US007074833B2

(12) United States Patent
Deregnaucourt et al.

(10) Patent No.: US 7,074,833 B2
(45) Date of Patent: *Jul. 11, 2006

(54) USE OF THE (1S,2R) ENANTIOMER OF MILNACIPRAN FOR THE PREPARATION OF A DRUG

(75) Inventors: Jean Deregnaucourt, Paris (FR); Richard Grosse, Gidy (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/805,940

(22) Filed: Mar. 22, 2004

(65) Prior Publication Data

US 2004/0259953 A1      Dec. 23, 2004

Related U.S. Application Data

(63) Continuation-in-part of application No. 10/453,574, filed on Jun. 3, 2003.

(30) Foreign Application Priority Data

Feb. 14, 2003  (FR) .................................. 03 01849
Feb. 16, 2004  (FR) ..................... PCT/FR04/00347

(51) Int. Cl.
    *A61K 31/165*    (2006.01)
(52) U.S. Cl. .................. 514/620; 514/613; 514/624; 514/659; 514/810; 514/811; 514/812; 514/813
(58) Field of Classification Search ................ 514/613, 514/620, 624, 659
    See application file for complete search history.

(56) References Cited

U.S. PATENT DOCUMENTS

| 4,478,836 | A  |    | 10/1984 | Mouzin et al. .............. 514/617 |
| 5,532,244 | A  | *  | 7/1996  | Wong et al. ............ 514/255.03 |
| 6,028,070 | A  | *  | 2/2000  | Heiligenstein ........... 514/238.8 |
| 6,184,222 | B1 | *  | 2/2001  | Heiligenstein ........... 514/239.2 |
| 6,602,911 | B1 |    | 8/2003  | Kranzler et al. ............ 514/624 |
| 6,635,675 | B1 | *  | 10/2003 | Kranzler et al. ............ 514/620 |
| 6,699,506 | B1 |    | 3/2004  | Paillard et al. |
| 2002/0010216 | A1 | * | 1/2002 | Rogosky et al. ............ 514/649 |
| 2003/0130353 | A1 | * | 7/2003 | Kranzler et al. ............ 514/620 |
| 2003/0139476 | A1 | * | 7/2003 | Kranzler et al. ............ 514/620 |
| 2003/0203055 | A1 | * | 10/2003 | Rao et al. .................... 424/738 |
| 2003/0232805 | A1 | * | 12/2003 | Kranzler et al. ............ 514/217 |
| 2004/0034101 | A1 | * | 2/2004 | Rao et al. .................... 514/619 |
| 2004/0122104 | A1 | * | 6/2004 | Hirsh et al. .................. 514/620 |
| 2005/0032782 | A1 | * | 2/2005 | Rao et al. .................... 514/220 |
| 2005/0096395 | A1 | * | 5/2005 | Rao et al. .................... 514/649 |

FOREIGN PATENT DOCUMENTS

| FR | 2759290 | 8/1998 |
| FR | 2759906 | 8/1998 |
| WO | WO09735574 | 10/1997 |
| WO | WO0126623 | 4/2001 |
| WO | WO0162236 | 8/2001 |
| WO | 03068211 | 8/2003 |
| WO | WO 04/030633 | 4/2004 |

OTHER PUBLICATIONS

STN/CAS online, file CAPLUS, Acc. No. 2000:737462, Doc. No. 134:246877 (Tsuruta et al., "Examination of drug—drug interaction of milnacipran hydrochloride in the presence of human P-450", Iyakuhin Kenkyu (2000), Vo. 31, No. 9, pp. 659-667) Abstract.*
Bonnaud et al., "1-Aryl-2-(aminomethyl)cyclopropanecarboxylic acid derivatives: A new series of potential antidepressant", J. Med. Chem. (1987), vol. 30, No. 2, pp. 318-325.*
W. Retz, et al.; European Neuropsychopharmacology, vol. 5-No. 3 (1995) pp. 296-297.
Index Merck No. 6281 (1996).
Moret et al., 1985 Neuropharmacology 24(12): 1211-1219.
Bonnaud et al., 1985, Journal of Chromatography, vol. 318: 398-403.
Shuto et al., Tetrahedron letters, 1996 vol. 37: 641-644.
Grard et al.,2000, Electrophoresis 2000 21: 3028-3034.
Doyle et al., 2001, Advanced Synthesis and Catalysis, vol. 343. 299-302.
Nores et al., 1987 Therapie 42: 555, 558.
Meador-Woodruff et al., 1988 J. Clim. Psychopharmacol. 8: 28-32.
Dictionnaire Vidal, 78 eme Edition, 2002.
The Diagnostic and Statistical Manual of Mental Disorders-IV(DSM-IV), 1995 A.P.A.
Deprez et al., European Journal of Drug Metabolism & Pharmacokinetics, 1998.
Spencer et al., Drugs, 1998.
Puozzo et al., European Journal of Drug Metabolism & Pharmacokinetics, 1998.
Viazzo et al., Tetrahedron letters, 1996 vol. 37: 4519-4522.
Shuto et al., Journal of Medicinal Chemistry, vol. 41, pp. 3507-3514, (1998).
Shuto et al., Journal of Med Chem, American Chem. Society, 1996, vo. 39: 4844-4852.
Shuto et al., Japanese Journal of Pharmacology, 2001, vol. 85, p. 207-213.

(Continued)

*Primary Examiner*—S. Mark Clardy
*Assistant Examiner*—Frank I. Choi
(74) *Attorney, Agent, or Firm*—Hueschen and Sage

(57) ABSTRACT

A method for treating or preventing a disorder or a condition by double inhibition of serotonin (5-HT) and noradrenaline (NA) reuptake in a subject in need thereof, while limiting the risks of cardiovascular disturbances and/or organ and/or tissue toxicity, comprising the step of administering to said subject a mixture of enantiomers of milnacipran enriched in the (1S,2R) enantiomer of milnacipran and/or of at least one of its metabolites, as well as their pharmaceutically-acceptable salts.

40 Claims, 4 Drawing Sheets

OTHER PUBLICATIONS

Hindmarch I., Human Psychopharmacology 2001 UK, vol. 16 p. S101-S104.
Baldwin D.S., Human Psychopharmacology 2001, vol. 16, p. S93-S99.
Artigas, "Selective Serotonin/Noradrenaline Reuptake Inhibitors", *CNS Drugs*, 1995, 4, 79-89.
Preskorn, et al., "Other Antidepressants", *Antidepressants: Past, Present and Future*, 2004, 264-311.
Preskorn, "Milnacipran: A Dual Norepinephrine and Serotonin Reuptake pump Inhibitor", *Journal of Psychiatric Practice*, 2004, 10, 119-126.
Yoshida, et al., "Elevation of blood pressure induced by high-dose milnacipran", *Hum. Psychopharmacol. Clin. Exp.*, 2002, 17, 431.
Schorderet, "Effets sur le système cardiovasculaire", Pharmacologie Des Concepts Fondamentaux Aux Applications Thérapeutiques, 1992, Chapter 25, pp. 363-364.
Ener, et al., "Serotonin Syndrome and Other Serotonergic Disorders", *Pain Medicine*, 2003, 4, 63-74.
Kolecki, "Isolated Venlafaxine-Induced Serotonin Syndrome", *J. Emerg. Med.*, 1997, 15, 491-493.
Hansen, et al., "Long-term antidepressive medication—an increased anesthetic risk?", *Der Anaesthesist*, 1990, 39, 205-210 (*Surgical Medline Extract*).
Thase, "Effects of Venlafaxine on Blood Pressure: A Meta-Analysis of Original Data from 3744 Patients", *J. Clin. Psychiatry*, 1998, 59, 502-508.
Partridge, et al., "A Depressed Myocardium", *Clinical Toxicology*, 2000, 38, 453-455.
Jordan, et al., "Influence of sibutramine on blood pressure: evidence from placebo-controlled trials", *Int. J. Obes. Relat. Metab. Disord.*, 2005, 29, 509-516 (*Medline Extract*)
Birkenfeld, et al., "Paradoxical effect of sibutramine of autonomic cardiovascular regulation", *Circulation*, 2002, 106, 2459-2465 (*Medline Extract*).
Sramek, et al., "Efficacy and safety of sibutramine for weight loss in obese patients with hypertension well controlled by beta-adrenergic blocking agents: a placebo-controlled, double-blind, radomised trial", *J. Hum. Hypertens.*, 2002, 16, 13-19 (*Medline Extract*).
Szabadi, et al., "The human pharmacology of reboxetine", *Hum. Psychopharmacol.*, 1998, *Suppl. 1*, S3-S12 (*Excerpta Medica Extract*).
Middleton, et al., "Evidence that imipramine-induced postural hypotension may be centrally mediated", *Hum. Psychopharmacol.*, 1998, 3, 181-190 (*Excerpta Medica Extract*).
Robinson, "Antidepressant Psychopharmacology: Current Limitations and Future Directions", *Primary Psychiatry*, 2003, 10, 43-49.
U.S. Appl. No. 10/623,431, filed Jul. 18, 2003, Kranzler et al.
U.S. Appl. No. 10/628,141, filed Jul. 24, 2003, Rao et al.
Caron, et al., *Eur. Neuropsychopharmacol*, "Acute electrophysiological effects of intravenous milnacipran, a new antidepressant agent", 1993, 3, 493-500.
Mills, *Crit. Care Clin.* "Serotonin Syndrome, A Clinical Update", 1997, 13, 763-783.
Palazidou, et al., "Rapid Reference to Depression", Jul., 2002, 42-59.

* cited by examiner

USE OF THE (1S,2R) ENANTIOMER OF MILNACIPRAN FOR THE PREPARATION OF A DRUG

The present invention concerns the use of a mixture of enantiomers enriched in the spatially configured (1S,2R) enantiomer of milnacipran and/or of at least one of its metabolites, as well as their pharmaceutically-acceptable salts, for the preparation of a drug intended to prevent or to treat disorders that can be managed by double inhibition of serotonin (5-HT) and noradrenaline (NA) reuptake, while limiting the risks of cardiovascular disturbances and/or of organ and/or tissue toxicity. More specifically, the mixture of enantiomers in accordance with the invention is intended to treat depression, chronic fatigue syndrome and urinary incontinence.

Milnacipran (Z(±)-2-(aminomethyl)-N,N-diethyl-1-phenylcyclopropanecarboxamide), a molecule synthesized at the PIERRE FABRE MEDICAMENT Research Centre (Castres, France), also called TN-912, dalcipran, minalcipran, midalcipran or midalipran is known to be a dual inhibitor of serotonin (5-HT) and noradrenaline (NA) reuptake. Milnacipran and its method of preparation are described in U.S. Pat. No. 4,478,836. Other information relating to milnacipran can be found in the twelfth edition of the Merck Index, as entry No. 6281.

Dual inhibitors of serotonin (5-HT) and noradrenaline (NA) reuptake correspond to a well-known class of antidepressant agents which selectively inhibit reuptake of both serotonin and noradrenaline. By way of example, venlafaxine and duloxetine are also dual inhibitors of serotonin and noradrenaline. Studies have shown that the ratio of noradrenaline reuptake inhibition to serotonin reuptake inhibition by milnacipran is approximately 2:1 (Moret et al., 1985 *Neuropharmacology* 24(12): 1211–1219; Palmier et al., 1989, *Eur J Clin Pharmacol* 37: 235–238).

U.S. Pat. No. 4,478,836 describes the use of milnacipran for the treatment of disorders of the central nervous system, in particular depression. Patent application WO01/26623 describes the use of milnacipran in association with phenylalanine and tyrosine in indications such as the treatment of fatigue, syndromes associated with pain, chronic fatigue syndrome, fibromyalgia and irritable bowel syndrome. Patent application WO01/62236 describes a composition containing milnacipran in association with one or several antimuscarinic agents in a large number of indications including depression. Application WO97/35574 describes a pharmaceutical composition containing milnacipran and idazoxan as an associated product for use simultaneously, separately or staggered in time to treat depression and its various forms, as well as disorders in which antidepressants are used. Milnacipran is also indicated for use in the treatment of urinary incontinence (FR 2 759 290).

The milnacipran molecule possesses two asymmetric carbons giving two different spatial configurations (1S,2R) and (1R,2S). These spatial configurations being non-superposable, the milnacipran molecule therefore exhibits optical isomerism.

Milnacipran hydrochloride thus exists in the form of two optically active enantiomers: the dextrorotatory enantiomer or Z-(1S,2R)-2-(aminomethyl)-N,N-diethyl-1-phenylcyclopropanecarboxamide hydrochloride and the levorotatory enantiomer Z-(1R,2S)-2-(aminomethyl)-N,N-diethyl 1-phenylcyclopropanecarboxamide hydrochloride. In its hydrochloride form, milnacipran (also called F2207) is currently marketed (IXEL, PIERRE FABRE MEDICAMENT, France) in the form of a racemic mixture as a serotoninergic and noradrenergic antidepressant agent. F2695 et F2696 designate the dextrorotatory (1S,2R) and levorotatory (1R,2S) enantiomers respectively of milnacipran hydrochloride (F2207):

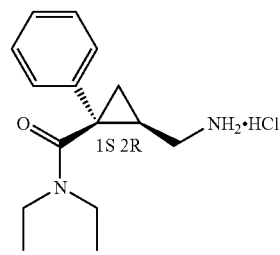

F2695

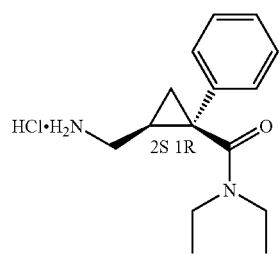

F2696

These two enantiomers can be separated and isolated using procedures described in the literature (Bonnaud et al., 1985, *Journal of Chromatography*, Vol. 318: 398–403; Shuto et al., *Tetrahedron letters*, 1996 Vol. 37:641–644; Grard et al., 2000, *Electrophoresis* 2000 21: 3028–3034; Doyle and Hu, 2001, *Advanced Synthesis and Catalysis*, Vol. 343: 299–302).

The inventors have now performed a pharmacokinetic study in man on the racemate and on the two enantiomers of milnacipran which uses enantiomer-selective assay methods. They have thus demonstrated the absence of racemization of the enantiomers in vivo.

Furthermore, although the racemate has been resolved, no analysis of the pharmacological and toxicological properties of the two enantiomers has been performed using modern, currently available methods such as cardiovascular measurements by telemetry, or genomic analyses for predictive pharmacotoxicology in vitro.

As with any active substance, antidepressants can induce adverse events or certain toxic effects that essentially derive from the pharmacological properties of these drugs, as well as from the dosage, from individual variations in patients (genetic polymorphism, organ-function insufficiency, gender, age) or from drug interactions. Antidepressants are thus the third most common class of products responsible for intoxication, after hypnotics and tranquillizers (Nores et al., 1987 *Thérapie* 42: 555–558). The risk of overdose with antidepressants is serious, since it can lead to death. Among the causes of acute intoxication with antidepressants should be mentioned accidental ingestion by children (all the more so since certain antidepressants are used in the treatment of enuresis), suicide attempts, accidental overdosage by phy sicians, concomitant medications in elderly patients, age-related physiological and pharmacokinetic changes (cardiac insufficiency, heptaic and/or renal insufficiency . . . ) and slowing down of metabolism whether genetic in origin or drug-induced (enzyme inhibition). After children, the elderly therefore represent the second at-risk population among patients treated. Elderly persons have higher plasma concentrations, related to reduced renal and/or hepatic clearance, and the risks of intoxication are more serious (Meadoer-Woodruff et al., 1988 *J. Clim. Psychopharmacol.* 8: 28–32).

The adverse side-effects, generally benign, which have been observed during treatment with milnacipran usually occur within the first week or the first two weeks of treatment and diminish thereafter, in parallel with improvement in the depressive episode. The most commonly-reported adverse events in single-drug therapy or in association with other psychotropics are dizziness, hypersudation, anxiety, hot flushes and dysuria. Certain less commonly reported adverse events are nausea, vomiting, dry mouth, constipation, tremor, palpitations, agitation, and cutaneous eruptions. Moreover, it is known that in patients with a history of cardiovascular disease or who concomitantly receive treatment for a cardiac condition, milnacipran can increase the incidence of cardiovascular adverse events (hypertension, hypotension, orthostatic hypotension, palpitations). In patents with high blood pressure or having heart disease it is therefore recommended to increase medical supervision since milnacipran in the form of a racemic mixture is likely to increase the heart rate. In those rare cases of overdose observed with milnacipran (at doses from 800 mg to 1 g) in single-drug therapy, the main symptoms observed are vomiting, respiratory disturbances and tachycardia (The Vidal Dictionary 78th edition, 2002). Another adverse event occasionally induced by milnacipran is elevated transaminase levels which may reflect a certain hepatic toxicity.

The at-risk populations that could potentially develop a certain number of adverse clinical manifestations during or following treatment with milnacipran are children, the elderly, patients with hepatic and/or renal insufficiency, patients receiving treatment that induces organ and/or tissue toxicity, in particular hepatic and/or renal toxicity, patients receiving treatment for a heart condition or that induces cardiovascular side-effects, patients with a history of cardiovascular disease and/or having cardiovascular disorders, especially those with disorders of cardiac rhythm, of blood pressure (hypo- or hypertensive patients) and patients suffering from heart disease.

Concerned to prevent, to an ever greater extent, the occurrence of possible side-effects that could constitute a danger, however small, to the health of patients treated with milnacipran, the inventors have now discovered that, surprisingly and unexpectedly, the (1S,2R) enantiomer of milnacipran, which is essentially responsible for the selective inhibitory activity on serotonin and noradrenaline reuptake, induced fewer side-effects of a cardiovascular nature and less organ and/or tissue toxicity, especially hepatic, than the racemic mixture. In particular, the inventors have discovered that, in dogs, administration of the (1S,2R) enantiomer of milnacipran leads to a lesser increase in heart rate and blood pressure, particularly diastolic blood pressure, than that which can be induced by administration of the racemic mixture. Moreover, the inventors have discovered that the (1S,2R) enantiomer of milnacipran hydrochloride (F2695) has a better profile of genomic toxicity than the (1R,2S) enantiomer of milnacipran hydrochloride (F2696) in an experimental model using primary rat hepatocytes. The inventors have also demonstrated that the (1R,2S) enantiomer (F2696) has a profile of genomic toxicity similar to that obtained with clomipramine, which is used as a reference psychotropic product known for its relative hepatic toxicity.

The object of the present invention is thus the use of a mixture of enantiomers of milnacipran enriched in the (1S,2R) enantiomer, preferentially the substantially pure F2695 enantiomer, as well as with their pharmaceutically-acceptable salts, for the preparation of a drug intended to prevent or to treat disorders or conditions that can be managed by double inhibition of serotonin (5-HT) and noradrenaline (NA) uptake, while limiting the risks of cardiovascular disturbances and/or while limiting the risks of organ and/or tissue toxicity.

The term "cardiovascular disturbances" is understood to refer to adverse cardiovascular side-effects of the drug administered alone or in association with other active substances.

For the purposes of the present invention, the phrase "side-effect" is understood to mean the foreseeable activity of a drug in an area other than that for which it is administered, that may be bothersome or undesirable when it limits the use of the drug.

The term "toxicity" is understood to mean the property of a drug to induce harmful effects on organs or tissue, in particular organs or tissues involved in the metabolism of milnacipran, especially hepatic and/or renal metabolism of milnacipran, and more specifically during the first pass of milnacipran in the liver. Preferentially, organ toxicity is cardiac toxicity and said tissue toxicity is hepatic and/or renal toxicity.

For the purposes of the present invention, the phrase "while limiting the risks of cardiovascular disturbances" or "while limiting the risks of toxicity" is understood to mean the fact of preventing these risks from increasing significantly in a patient following administration of the drug.

For the purposes of the present invention, the term "(1S, 2R) enantiomer of milnacipran" designates the (1S,2R) enantiomer of milnacipran, as well as its pharmaceutically-acceptable salts. Preferentially, this is the (1S,2R) enantiomer of milnacipran hydrochloride (F2695). "(1R,2S) enantiomer of milnacipran" designates the (1R,2S) enantiomer of milnacipran, as well as its pharmaceutically-acceptable salts such as the hydrochloride (F2696). "Racemic mixture" designates a 50:50 mixture by weight of the (1S,2R) enantiomer of milnacipran and the (1R,2S) enantiomer of milnacipran, as well as their pharmaceutically-acceptable salts.

For the purposes of the present invention, "mixtures of the enantiomers of milnacipran enriched in the (1S,2R) enantiomer" signifies a mixture of the (1S,2R) enantiomer and the (1R,2S) enantiomer of milnacipran in which the mass/mass ratio of the (1S,2R) enantiomer to the (1R,2S) enantiomer is greater than 1:1. In the mixture of the enantiomers of milnacipran enriched in the (1S,2R) enantiomer, the mass/mass ratio of the (1S,2R) enantiomere to the (1R,2S) enantiomer is advantageously greater than or equal to 55:45, more advantageously greater than 60:40, yet more advantageously greater than 65:35, yet more advantageously greater than 70:30, yet more advantageously greater than 75:25, yet more advantageously greater than 80:20. Produced in a particularly advantageous mode, the mass/mass ratio of the (1S,2R) enantiomer to the (1R,2S) enantiomer is greater than 82:18, in a more advantageous manner greater than 84:16, in an even more advantageous manner greater than 86:14, in an even more advantageous manner greater than 88:12, in an even more advantageous manner greater than 90:10. Produced in a preferred mode, the mass/mass ratio of the (1S,2R) enantiomer to the (1R,2S) enantiomer is greater than 91:9, in a more preferred manner greater than 92:8, in an even more preferred manner greater than 93:7, in an even more preferred manner greater than 94:6, in an even more preferred manner greater than 95:5, in an even more preferred manner greater than 96:4, in an even more preferred manner greater than 97:3, in an even more preferred manner greater than 98:2, in an even more preferred manner greater than 99:1, in an even more preferred manner greater than 99.5:0.5. In a particularly preferred manner, the mixture of enantiomers of milnacipran enriched in the (1S,2R) enantiomer is substantially pure, that is to say, containing approximately 100% (1S,2R) enantiomers by weight.

The use of metabolites also enters into the scope of the present invention, preferentially the metabolites of milnacipran that are active in vivo, and their pharmaceutically-acceptable salts, such as:

the hydrochloride of Z-(±)phenyl-1-aminomethyl-2-cyclopropane-carboxylic acid (F1567):

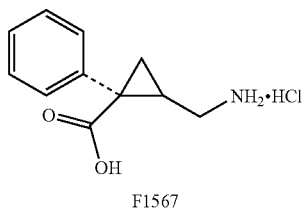

F1567

Molecular mass: 277.7 Characteristics: white crystals Melting point: 230° C. Plate chromatography: medium: silica Solvent: Butanol/ethanol/water (6/2/2) Developer: Ultraviolet and ninhydrine Rf: 0.6

(±)phenyl-3 methylene-34 pyrrolidone-3 (F1612):

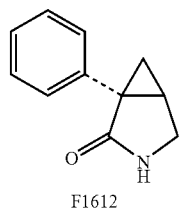

F1612

Molecular mass: 173.2 Characteristics: white crystals Melting point: 70° C. Plate chromatography: medium: silica Solvent: Benzene/dioxane/ethanol (90/25/4) Developer: Ultraviolet and iodine Rf: 0.46 the hydrochloride of Z(±)-(para-hydroxyphenyl)-1-diethylaminocarbonyl-1-aminomethyl-2-cyclopropane (F2782):

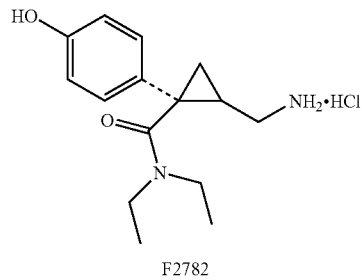

F2782

Molecular mass: 298.82 Characteristics: white crystals Melting point: 250° C. Plate chromatography: medium: silica Solvent: Butanol/ethanol/water (6/2/2) Developer: Ultraviolet and iodine-ninhydrine Rf: 0.42 the oxalate acid of Z(±)-phenyl-1-ethylaminocarbonyl-1-aminomethyl-2-cyclopropane (F2800):

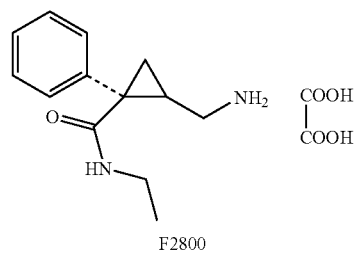

F2800

Molecular mass: 308.33 Characteristics: white crystals Melting point: 150° C. Plate chromatography: medium: silica Solvent: CHCl$_3$/methanol/NH$_4$OH (90/9/1) Developer: Ultraviolet and ninhydrine Rf: 0.40 the hydrochloride of Z(±)-phenyl-1-aminocarbonyl-1-aminomethyl-2-cyclopropane (F2941)

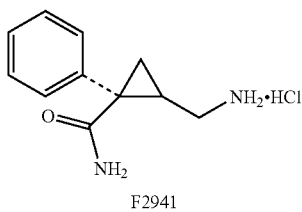

F2941

Molecular mass: 226.74 Characteristics: white crystals Melting point: 245° C. Plate chromatography: medium: silica Solvent: CHCl$_3$/methanol/NH$_4$OH (80/18/2) Developer: Ultraviolet and ninhydrine Rf: 0.30

These metabolites have, just as milnacipran has, two asymmetric carbons giving two different spatial configurations (1S,2R) and (1R,2S). These spatial configurations being non-superposable, these metabolites also exhibit optical isomerism. The ratio of the two enantiomers of the metabolite of milnacipran in the mixture of enantiomers is as described above for enantiomers of milnacipran.

The present invention covers therefore these active metabolites, their enantiomers, as well as their pharmaceutically-acceptable salts, in addition to their use as a drug in the treatment of the disorders described in the present patent such as depression, pain, fibromylalgia and urinary incontinence. The metabolites in accordance with the invention are in the form of racemates or preferentially in the form of a mixture of enantiomers enriched in the most active (1S,2R) enantiomer. In a preferable manner, the active metabolite used comes from the F2695 enantiomer and is the (1S,2R) enantiomer of the active metabolite. In a more preferable manner, this is the (1S,2R) enantiomer of the hydrochloride of Z-(para-hydroxyphenyl)-1-diethylaminocarbonyl-1-aminomethyl-2-cyclopropane (F2782). The term "active metabolite" is understood to designate a derivative resulting from the metabolisation of milnacipran in vitro or in vivo and having the capacity to inhibit reuptake of serotonin and of noradrenaline; preferentially, these are F2782, F2941, F2800, F1612 and F1567.

The object of the present invention is therefore the use of a mixture of enantiomers preferentially enriched in the (1S,2R) enantiomer of at least one metabolite of milnacipran, preferentially chosen among F2782, F2941, F2800, F1612 and F1567, as well as their pharmaceutically-acceptable salts, for the preparation of a drug intended to prevent or to treat disorders or conditions that can be managed by double inhibition of reuptake of serotonin (5-HT) and of noradrenaline (NA), while limiting the risks of cardiovascular disturbances and/or while limiting organ and/or tissue toxicity, in particular, cardiac, hepatic and/or renal toxicity.

The use of a mixture of enantiomers milnacipran enriched in the (1S,2R) enantiomer, preferentially the substantially pure F2695 enantiomer, and at least one of its metabolites, preferably chosen among F2782, F2941, F2800, F1612 and F1567, preferentially enriched in the (1S,2R) enantiomer, for the preparation of a drug intended to prevent or to treat disorders or conditions that can be managed by double inhibition of reuptake of serotonin (5-HT) and of noradrenaline (NA), while limiting the risks of cardiovascular disturbances and/or while limiting organ and/or tissue toxicity, in particular, cardiac, hepatic and renal toxicity also enters into the scope of the present invention.

"Pharmaceutically-acceptable salt" designates all salts that retain the efficacy and properties of an active substance and that do not cause side effects. Preferentially, these are pharmaceutically-acceptable salts of mineral or organic acids. By way of example, but not limited to these, halohydrates such as the hydrochloride and the bromohydrate, the fumarate, the maleate, the oxalate, the citrate, the methanesulfonate, the glutamate, the tartrate, the mesylate and their possible hydrates should be mentioned.

For the purposes of the present invention, the term "mixture of enantiomers" signifies the mixture of enantiomers of milnacipran enriched in the (1S,2R) enantiomer, as well as their pharmaceutically-acceptable salts, and/or the mixture of enantiomers of at least one of the metabolites of milnacipran, preferentially enriched in the (1S,2R) enantiomer, as well as their pharmaceutically acceptable salts.

The mixture of enantiomers in accordance with the invention, preferentially substantially-pure F2695 enantiomer, is administered to all types of patients requiring such treatment, whether it be for therapeutic and/or prophylactic purposes. For therapeutic purposes, the aim is to eradicate or to improve the condition to be treated and/or one or more related symptoms. For prophylactic purposes, the aim is to prevent the appearance of the condition to be treated and/or of one or more related symptoms. Nevertheless, the mixture of enantiomers in accordance with the invention is particularly adapted to populations of at-risk patients who may be likely to develop certain adverse clinical manifestations during or following treatment with milnacipran in the racemic form. These are principally children, the elderly, patients with hepatic and/or renal insufficiency, patients receiving treatment that induces hepatic and/or renal organ and/or tissue toxicity, patients receiving treatment for a heart condition, patients receiving treatment that induces cardiovascular side-effects, patients with a history of cardiovascular disease (for example, myocardial infarctus) and/or having cardiovascular disorders, such as patients with cardiac rhythm disorders (tachycardia, bradycardia, palpitations), patients with blood pressure disorders (hypo- or hypertensive patients) or patients suffering from heart disease.

Among the numerous disorders or conditions that have as symptoms cardiac rhythm disorders and for which the present invention is particularly well-adapted in the treatment of at-risk patients who suffer from them, tachycardia which corresponds to an acceleration of the rhythm of the heart beat (tachycardia is moderate when the heart rate is from 80 to 100 beats per minute, severe when it exceeds 100), palpitations, extrasystoles (sporadic, frequent or during myocardial infarctus), auricular fibrillation, flutter and auricular tachysystole, bradycardia, cardiac insufficiency, and myocardial infarctus should be mentioned.

Among the numerous disorders or conditions that have as symptoms blood pressure disorders and for which the present invention is particularly well-adapted in the treatment of at-risk patients who suffer from them, arterial hypertension, malignant arterial hypertension, pulmonary arterial hypertension, portal hypertension, paroxysmal essential hypertension, hypotension, orthostatic hypotension and intra-cranial hypertension should be mentioned.

Advantageously, those cardiovascular disorders for which the risks can be limited by the administration of the mixture of enantiomers in accordance with the invention, and preferentially by the administration of the substantially-pure F2695 enantiomer, are as follows:
  elevated diastolic and/or systolic blood pressure measured in millimeters of mercury (mmHg); more specifically, this is an increase in diastolic blood pressure, and/or,
  cardiac rhythm disorders, in particular, an increase in the patient's heart rate.

Systolic blood pressure is the maximal value for blood pressure, and it corresponds to the moment when the first heart sound is heard in the humeral artery during measurement of blood pressure. The systole is the interval of the cardiac cycle during which the heart cavities contract, causing expulsion of the blood. Diastolic blood pressure is the minimal value of blood pressure, corresponding to the disappearance of heart sounds in the humeral artery when the cuff of the sphygmomanometer is deflated during measurement of blood pressure. The diastole is the interval of the cardiac cycle during which the heart cavities fill with blood. Elevation of systolic and/or diastolic pressure means increased blood pressure which is characteristic of systemic arterial hypertension (and its variant forms), the symptoms of which may be the following: headache, fatigue, mild sensorial disturbances such as dizziness, buzzing in the ears, palpitations, nosebleed, confusion or drowsiness, cramps, numbness or tingling in the feet and hands. Systemic arterial hypertension (and its variant forms) can lead to serious, indeed fatal, complications: cerebral vascular accidents, left ventricular heart failure, kidney failure, ischemic heart diseases (myocardial infarctus, angor and their variant forms). According to current guidelines, a patient is considered to have arterial hypertension when his/her diastolic blood pressure is above 90 mmHg and his/her systolic blood pressure is above 140 mmHg.

The toxicity for which the risks can be limited by the administration of the mixture of enantiomers in accordance with the invention is advantageously organ toxicity, particularly cardiac toxicity, and/or tissue toxicity, in particular hepatic and/or renal toxicity. Tissue toxicity may be revealed by the presence of icterus or by laboratory markers.

The use of the mixture of enantiomers in accordance with the invention in veterinary medicine for the treatment of animals, in particular household pets or breeding animals that require such treatment also enters into the scope of the present invention.

Because of their pharmacological properties, in particular as dual inhibitors of serotonin (5-HT) and noradrenaline (NA) reuptake, the mixture of enantiomers is especially useful in the preparation of drugs intended for preventive and/or curative treatment of a number of disorders and conditions (syndromes) described hereinafter, while limiting the risks of cardiovascular disturbances and/or while limiting organ and/or tissue toxicity, in particular cardiac, hepatic and/or renal toxicity.

Among these disorders or conditions, disorders of the central nervous system as defined in "*The Diagnostic and Statistical Manual of Mental Disorders—IV (DSM-IV)*, 1995 *American Psychiatric Association*" should be mentioned. By way of example, but not limited to these, the following disorders and conditions should be mentioned: depression, in particular deep depression, resistant depression, depression in the elderly, psychotic depression, depression induced by treatment with interferon, depressive state, manic-depressive syndrome, seasonal depressive episodes, depressive eposides related to general health status, depressive episodes related to mood-altering substances, bipolar disease, schizophrenia, generalized anxiety, morose and marasmic states, stress-related diseases, panic attacks, phobias, in particular agoraphobia, obsessive-compulsive disorders, behavioral disorders, oppositional disorders, post-traumatic stress disorder, depression of the immune system, fatigue and accompanying pain syndromes, chronic fatigue syndrome, fibromyalgia, and other functional somatic disorders, autism, disorders characterized by attention deficit due to general health status, attention disorders due to hyperactivity, eating disorders, neurotic bulimia, neurotic anorexia, obesity, psychotic disorders, apathy, migraine, pain and in particular chronic pain, irritable bowel syndrome, cardiovascular diseases and in particular anxiety-depressive syndrome in myocardial infarctus or in hypertenison, neurodegenerative diseases and related anxiety-depressive syndromes (Alzheimer's disease, Huntington's chorea, Parkinson's disease), urinary incontinence, in particular urinary incontinence related to stress and enuresis, drug addition and in particular anxiety addition to tobacco, in particular to nicotine, to alcohol, to narcotics, to drugs, to analgesics used in weaning-off from these addictive states.

More specifically, the object of the present invention concerns the use of a mixture of enantiomers in accordance with the invention, preferentially the substantially-pure F2695 enantiomer, for the preparation of a drug intended to treat or to prevent depression or depressive state while limiting the risks of cardiovascular disturbances and/or while limiting organ and/or tissue toxicity, in particular hepatic and/or renal toxicity. In the context of the present invention, the term "depression" is understood to refer to a constellation of symptoms having, on the one hand, a psychological aspect consisting of mood disorders with pessimism, moral suffering, thoughts of death or suicide, mental inhibition, and on the other hand, a physical aspect of motor deficit, consisting in particular of a slowdown in motor activity, of appetite disturbances, of constipation, of sleep disturbances and of weight-control disturbances. Depression therefore corresponds to a pathological psychological state combining a painful mood-alteration and a reduction in mental and motor activity. The term "depressive state" is understood to refer to a mental state characterized by a decline in neuropsychological tonicity, manifesting as lassitude, tendency to fatigue, discouragement and tendency to pessimism sometimes accompanied by anxiety.

Furthermore, the object of the present invention concerns more specifically the use of a mixture of enantiomers in accordance with the invention, preferentially the substantially-pure F2695 enantiomer, for the preparation of a drug intended to prevent or to treat fibromyalgia and/or chronic fatigue syndrome while limiting the risks of cardiovascular disturbances and/or while limiting organ and/or tissue toxicity, in particular hepatic and/or renal toxicity. Fibromyalgia syndrome is a chronic syndrome characterized by a feeling of pain and burning with morning stiffness mainly affecting articular and peri-articular fibrous tissues, and by a feeling of deep fatigue. Fibromyalgia includes a constellation of symptoms. The most frequent are non-restorative sleep, headache, digestive disturbances, depressive state, muscle spasm, facial pain, numbness etc. Chronic fatigue syndrome is characterized by a state of exhaustion or of fatigue. The most common symptoms are a state of weakness, spasms and/or muscle pain, excessive need for sleep, fever, angina, memory loss and/or difficulty concentrating, insomnia, depression.

In addition, the object of the present invention concerns more specifically the use of a mixture of enantiomers in accordance with the invention, preferentially the substantially-pure F2695 enantiomer, for the preparation of a drug intended to prevent or to treat pain and in particular chronic pain while limiting the risks of cardiovascular disturbances and/or while limiting organ and/or tissue toxicity, in particular hepatic and/or renal toxicity. Pain may be associated with various disorders and/or wounds. It may be acute or chronic. Epidemiological studies have demonstrated the relations between states of chronic pain and anxiety and depression. Thus, patients suffering from chronic pain may develop emotional problems that lead to depression, and, in the worse cases, to a suicide attempt. A patient is considered to be in chronic pain if he/she complains of suffering for a period of more than six months. Among the various forms of chronic pain, the following should be mentioned by way of example, but not limited to these: pain associated with fibromyalgia and/or arising in fibrous tissues, muscles, tendons, ligaments and other sites, abdominal pain and diarrhea in irritable bowel syndrome, as well as lower back pain.

In addition, the object of the present invention concerns more specifically the use of a mixture of enantiomers in accordance with the invention, preferentially the substantially-pure F2695 enantiomer, for the preparation of a drug intended to prevent or to treat urinary incontinence and in particular urinary incontinence related to stress and enuresis, while limiting the risks of cardiovascular disturbances and/or while limiting organ and/or tissue toxicity, in particular hepatic and/or renal toxicity.

Prophylactic and therapeutic treatment of the abovementioned disorders is achieved by administering to an animal, preferably to man, a therapeutically-effective quantity of a mixture of enantiomers in accordance with the invention, preferentially the substantially-pure F2695 enantiomer, alone or in association with at least one other active substance. In most cases, this concerns man, however the treatment is also adapted to animals, in particular breeding animals (livestock, rodents, poultry, fish, . . . ) and to domestic animals (dogs, cats, rabbits, horses, . . . ).

The mixture of enantiomers, enriched in the (1S,2R) enantiomer, of milnacipran and/or of at least one of its metabolites, as well as their pharmaceutically-acceptable salts, as previously described, is advantageously administered to patients receiving simultaneously, separately or staggered in time at least one other active compound in the treatment of the abovementioned disorders.

Preferentially, the object of the present invention also includes, for use as a drug:
  a) the said mixture of enantiomers enriched in the (1S,2R) enantiomer of milnacipran and/or of at least one of its metabolites as well as their pharmaceutically-acceptable salts, and
  b) at least one active compound chosen among the psychotropics, in particular antidepressants, and antimuscarinic agents, as associated products for use simultaneously, separately or staggered in time in the treatment or the prevention of depression, in particular deep depression, resistant depression, depression in the elderly, psychotic depression, depression induced by treatment with interferon, depressive state, manic-depressive syndrome, seasonal depressive episodes, depressive episodes related to general health status, depressive episodes related to mood-altering substances.

The term "psychotropic" is understood to designate a substance of natural or artificial origin capable of modifying mental activity and whose action is essentially exerted on the central nervous system and the psychological state. Psychotropics are divided into three groups: 1) psycholeptics (hypnotics, neuroleptics and anxiolytics), 2) psychoanaleptics (antidepressants and psychotonics) and 3) psychodysleptics (hallucinogenics).

Preferably, the said psychotropic is an antidepressant. By way of example, but not limited to these, the antidepressant is chosen among (i) monoamine oxidase inhibitors (MAOIs) such as iproniazid, pargyline, selegine, (ii) 5HT1D-agonists such as sumatriptan, adrenaline and noradrenaline (alpha and beta sympathomimetics) (iii) tricyclic antidepressants, such as imipramine, clomipramine, (iv) selective serotonin reuptake inhibitors (SSRIs) such as fluoxetine, (v) selective noradrenaline reuptake inhibitors, such as for example tandamine, fluparoxan, mirtazapine (vi) serotonin and noradrenaline reuptake inhibitors, such as venlafaxine and duloxetine. By way of example, but not limited to these, the antimuscarinic agent is chosen among tolterodine, propiverine, oxybutynin, trospium, darifenacine, temiverine, ipratropium.

Preferably, the object of the present invention also includes for use as a drug:
  a) the said mixture of enantiomers enriched in the (1S,2R) enantiomer of milnacipran and/or of at least one of its metabolites as well as their pharmaceutically-acceptable salts, and
  b) at least one other active substance chosen among the active compounds inducing organ toxicity and the active compounds inducing tissue toxicity, in particular hepatic and/or renal toxicity or with one or more active substances intended for treatment of hepatic or renal insufficiency, as associated products for use simultaneously, separately or staggered in time in the treatment or the prevention of conditions or disorders that can be managed by double inhibition of serotonin (5-HT) and noradrenaline (NA) reuptake.

Preferably, the object of the present invention also includes, for use as a drug:
  a) the said mixture of enantiomers enriched in the (1S,2R) enantiomer of milnacipran and/or of at least one of its metabolites as well as their pharmaceutically-acceptable salts, and
  b) at least one other active substance chosen among active compounds inducing cardiovascular side-effects or compounds given to treat a heart condition, as associated products for use simultaneously, separately or staggered in time in the treatment or the prevention of conditions or disorders that can be managed by double inhibition of serotonin (5-HT) and noradrenaline (NA) reuptake.

Advantageously, the cardiovascular side-effects induced are those mentioned previously, and more specifically, arterial hypertension, hypotension, cardiac rhythm disorders (tachycardia, bradycardia, palpitations).

The object of the present invention also includes pharmaceutical compositions containing the associated products previously described.

In the context of the present invention, the mixture of enantiomers in accordance with the invention, preferentially the substantially-pure F2695 enantiomer, is advantageously administered, but not in a limited manner, via the oral route, the nasal route, the transdermal, rectal, intestinal or parenteral route, by intramuscular, subcutaneous or intravenous injection, alone or in association with other active substances, as previously described.

When administered alone, the mixture of enantiomers in accordance with the invention, preferentially the substantially-pure F2695 enantiomer, may be administered per se or in the form of a pharmaceutical composition in which the said mixture of enantiomers or of their pharmaceutically-acceptable salts, is combined or mixed with one or several media, pharmaceutically-acceptable excipients and/or diluents, particularly to enhance bioavailability.

When the mixture of enantiomers in accordance with the invention, and preferentially the substantially-pure (1S,2R) F2695 enantiomer of milnacipran, is administered in association with other active substances, the said mixture and the other active substances may be formulated as a mixture or separately in an identical or different form. They may be administered via the same or a different route.

The pharmaceutical compositions in accordance with the invention may be formulated in a conventional manner well-known to the person skilled in the art using one or more physiologically-acceptable media including excipients, adjuvants and additives such as for example preservatives, stabilizers, wetting agents or emulsifiers. The method of formulation chosen depends on the desired route of administration.

In the context of administration by injection, an aqueous solution is advantageously used, in particular a physiologically-acceptable buffer solution, such as Hank's solution, Ringer's solution or physiological saline solution. In the context of transdermal administration or via the mucous membranes, penetrating agents appropriate to the mucous membrane to be crossed are advantageously used. Such penetrating agents are well known to the person skilled in the art. In the context of oral administration, the pharmaceutical compositions in accordance with the invention are advantageously administered in unit-dose or multiple-dose administration forms in mixtures containing appropriate pharmaceutical media known to the person skilled in the art. Appropriate unit-dose administration forms include in particular tablets, possibly scored, capsules, powders, granules, oral solutions or suspensions, and aerosols. Appropriate multiple-dose administration forms include in particular drinkable drops, emulsions and syrups.

In the preparation of tablets, the mixture of enantiomers in accordance with the invention, preferentially the substantially-pure F2695 enantiomer, is formulated with a pharmaceutically-acceptable vehicle such as in particular polyvinylpyrrolidone, carbopol gal, polyethylene glycol, gelatine, talc, starch, lactose, magnesium stearate, gum arabic or their analogs. By way of example, the tablet contains the following excipients: calcium hydrogen phosphate dihydrate, calcium carmellose, povidone K30, anhydrous colloidal silicon dioxide, magnesium stearate, talc. The tablets may also be coated, that is to say, covered with several coats of various substances such as saccharose in order to facilitate swallowing or preservation. The coating may also contain dyes or colorants in order to differentiate and to characterize the tablets with regard to their dosage strength, for example. The tablets may also be presented in a more or less complex formulation intended to modify the rate of release of the active substance. Release of the active substance of the said tablet may be rapid, sustained or delayed depending on the desired absorption. Thus, the mixture of enantiomers in accordance with the invention, preferentially the substantially-pure F2695 enantiomer, may be prepared in a pharmaceutical form for sustained release obtained according to the process described in patent EP 939 626. This pharmaceutical form is presented in the form of multiparticles containing a large number of mini-granules and has a certain release profile in vitro.

Release of the mixture of enantiomers in accordance with the invention may be delayed and/or controlled by using an implant or by transdermal delivery, in particular subcutaneous or intramuscular, by intramuscular injection or by a transdermal patch. The said mixture is then formulated, in particular, with appropriate hydrophobic or polymeric substances and ion-exchange resins.

The quantity of the mixture of enantiomers in accordance with the invention, preferentially the substantially-pure F2695 enantiomer, to be administered to the patient depends on the condition to be treated, the desired effect, in particular a therapeutic or prophylactic effect, the health status and age of the patient, in particular his/her medical history of cardiovascular disease, the conditions of treatment and the method of administration of the drug. The quantities required to be administered for effective therapeutic or prophylactic use in a human patient can be determined based on animal models or on data, known to the person skilled in the art, obtained during the treatment of depression in man, for example, using a racemic mixture of milnacipran.

In the context of therapeutic and/or prophylactic treatment of the disorders mentioned above, and in particular depression, depressive states, fibromyalgia, chronic fatigue syndrome, pain, the drug in accordance with the invention is advantageously administered at doses from 0.01 mg to 10 mg/kg body weight per day in one or more intakes, more advantageously at doses from 0.05 mg to 5 mg/kg body weight per day in one or more intakes, and even more advantageously at doses from 0.1 mg to 1 mg/kg body weight per day in one or more intakes. In a particularly advantageous manner, administration of the said medicinal product at such doses as those defined above is divided into two daily intakes, preferentially in capsule form. By way of example, the mixture of enantiomers in accordance with the invention, preferentially the substantially-pure F2695 enantiomer, is advantageously administered in the form of a capsule containing approximately 6.75 mg of active substance per capsule, 12.5 mg/capsule, 25 mg/capsule, 50 mg/capsule.

Other characteristics, aims and advantages of the invention will become apparent in the examples that follow. The invention is not limited to these particular examples which are provided simply by way of example and which should be read in comparison with the following figures:

EXAMPLES

Example No. 1

Figure 1:
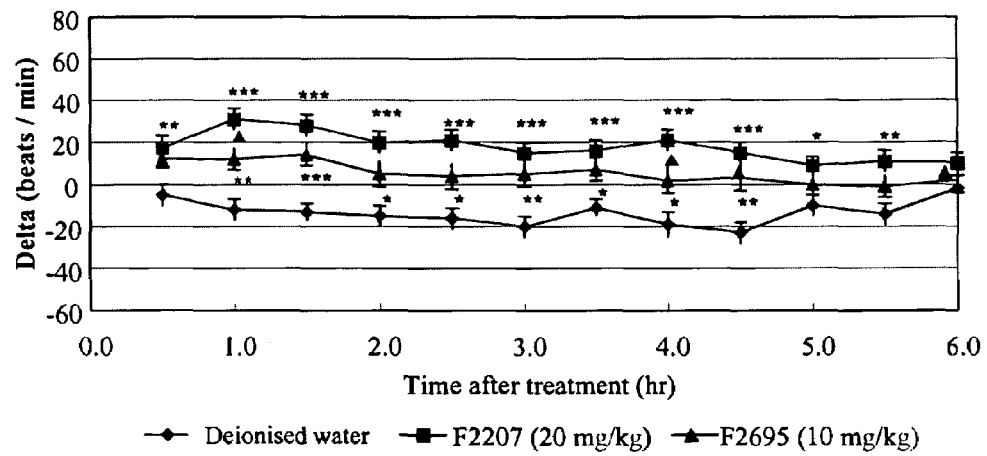
FIG. 1: Change in heart rate following single administration (delta values):
***: $p \leq 0.001$ versus deionized water
**: $p \leq 0.01$ versus deionized water
*: $p \leq 0.05$ versus deionized water
Δ: $p \leq 0.05$ versus F2207

Pharmacokinetic Studies on Milnacipran and on its Enantiomers

Pharmcokinetic studies on milnacipran hydrochloride (F2207) and on its enantiomers (F2695 and F2696) were performed in various animal species and in man.

In animals, the pharmacokinetics of each enantiomer were studied following administration of the racemate or of one single enantiomer. Plasma concentrations of the F2695 and F2696 enantiomers are approximately equivalent in the animal species tested (monkey and rat).

A pharmacokinetic study in man involving 12 healthy subjects was performed by administering the racemate or one of the two enantiomers alone. It was shown that the pharmacokinetic profile of each enantiomer is independent of whether it was administered separately or in the form of the racemate, indicating the absence of interaction between the enantiomers (Table 1).

TABLE 1

Table of the main pharmacokinetic variables of milnacipran hydrochloride (F2207) and its two enantiomers F2695 et F2696.

| Dose administered (mg) | F2207 (50 mg) | | F2695 (D) (25 mg) | F2696 (L) (25 mg) |
|---|---|---|---|---|
| | F2695 (D) | F2696 (L) | | |
| Cmax (nmol · l$^{-1}$) | 214 | 179 | 216 | 212 |
| Tmax (hours) | 3.42 | 2.87 | 3.08 | 2.21 |
| AUC 0→∞ (nmol · h · l$^{-1}$) | 2896 | 1563 | 2869 | 1543 |
| T½ (hours) | 9.28 | 5.75 | 9.38 | 5.58 |

Cmax: Maximal plasma concentration directly estimated based on experimental data
Tmax: Time to reach maximal plasma concentration
AUC$_{0\to\infty}$: Area under the curve for plasma concentrations in relation to time extrapolated to infinity
T½: Terminal half-life of decrease in plasma concentrations These findings indicate that no biotransformation of the F2695 or F2696 enantiomers was detected in the species studied.

Example No. 2

Biochemical Studies of Milnacipran and of its Enantiomers

The two enantiomers (F2695 and F2696) of milnacipran hydrochloride (F2207) were studied in vitro on uptake of noradrenaline and serotonin as well as on binding of paroxetine in the rat brain.

2.1. Materials and Methods 2.1.1. Noradrenaline Uptake by a Homogenate (P$_2$) of Rat Hypothalamus Preparation du P2

Male Sprague-Dawley rats, from 200 to 300 g, were stunned and decapitated, and the hypothalami were rapidly removed. Two hypothalami are homogenized in 4 ml of sucrose 0.32 M on Potter S by 16 complete passes back and forth at 800 rpm, then centrifuged for 10 min at 1000 g to eliminate cell debris. The supernatant is centrifuged for 20 min at 10 000 g and the P$_2$ thus obtained is recovered in 4 ml of sucrose 0.32 M and homogenized on a Dounce.

Uptake $^3$H-(1)-NA: 13 Ci/mmol (Amersham) is used.

Uptake takes place in a phosphate buffer (containing 8 g of NaCl, 1.21 g of K$_2$HPO$_4$ and 0.34 g of KH$_2$PO$_4$ per liter) pre-oxygenated 30 min before use with a mixture of O$_2$/CO$_2$ (95%/5%).

In 5-ml plastic tubes placed in a water bath at 37° C., the following are introduced:

100 μl of buffer or inhibitor,
700 μl of buffer (containing 25 μM of pargyline),
μl of P$_2$.

After temperature balance, the reaction begins by the addition of 100 μl of $^3$H-NA, 50 nM final concentration.

Exactly 10 min later, the reaction is stopped by adding 2.5 ml of chilled buffer and filtering through GF/F filters. The tube is then rinsed once and the filter once with 2.5 ml of chilled buffer. The filter is then introduced into a Beckman mini-vial and, after adding 3 ml of Instagel (Packard) liquid scintillator, radioactivity is measured with a Tricarb Packard liquid scintillation counter.

Nonspecific uptake (NS) is measured as the presence of DMI 10$^{-5}$ M.

The percentage of inhibition is calculated using the formula:

$$\frac{(\text{total uptake} - NS) - (\text{uptake in the presence of inhibitor} - NS)}{(\text{total uptake} - NS)}$$

The IC$_{50}$ is determined graphically on the mean curve of percentage inhibition (4 assays) in relation to the log of the concentration of inhibitor.

2.1.2. Serotonin Uptake

The method was developed following that of Gray and Whittaker (1962, *J Anat.*, 96: 79–97). After homogenization of brain tissue in a sucrose solution, the presynaptic terminals break away from the axon and close to form synaptosomes obtained by subcellular fractionation.

Male Sprague-Dawley (Janvier) rats weighing 180–200 g were used. After sacrifice of the animal, the hypothalamus was removed, weighed and homogenized on a Dounce in 0.32 M sucrose at 0° C.

This homogenate was centrifuged for 10 min at 1000 g (2400 rpm—Hettich, Rotenta). The supernatant was recovered and centrifuged for 20 min at 10 000 g (8000 rpm—Beckam, model J2–21 M: rotor J14). The residue (called the P$_2$ fraction) was recovered in sucrose at a concentration of 50 mg/ml.

The following were incubated for 5 min at 37° C.:

350 μl of chilled buffer (NaCl 136 mM, KH$_2$PO$_4$ 2.4 mM, K$_2$HPO$_4$ 6.9 mM, pH 7.2) preoxygenated 30 min before,
50 μl of membranes (5 mg/ml finally),
50 μl of citalopram (10$^{-5}$ M finally) for nonspecific uptake,
50 μl of $^3$H-5-HT (50 nM finally) (NEN, France, 28.4 Ci/mmol).

Exactly 5 min after the start of incubation, the reaction was stopped by vacuum filtration on Whatman GF/F filters (predilution with 2.5 ml of chilled buffer then rinsing with 3 times 2.5 ml).

The radioactivity collected on the filter was measured (Packard Tricarb 4640) by liquid scintillation with Emulsifier-Safe (Packard).

The IC$_{50}$ were determined by transposing the percentages of inhibition onto a graph in relation to the log of the product concentration (6 concentrations in duplicate).

2.1.3. Paroxetine Binding

Male Sprague-Dawley rats (Janvier) weighing 180–200 g were used. The hypothalami of several rats were collected and homogenized in 5 ml of chilled buffer (50 mM Tris-HCl, 120 mM NaCl, 5 mM KCl, pH 7.5) on a Dounce, and the homogenate was centrifuged at 30 000 g (27 000 rpm—Beckman. L5-50E, rotor T40) for 10 min. The residue obtained was recovered in 5 ml of buffer and recentrifuged under the same conditions. The new residue was recovered in the same buffer and finally rehomogenized on a Dounce at a tissue concentration of 10 mg/ml. The membrane suspension (100 l) was incubated with 3H-paroxetine (NEN, France, 28.6 Ci/mmol) at a concentration (final) of 0.1 nM, at 20° C., in a final volume of 1 ml for 2 h. After 2 h incubation, the reaction was stopped by vacuum filtration on Whatman GF/F filters pretreated in a 0.05% solution of polyethylenimine 30 min beforehand (predilution with 4 ml of chilled buffer, then the tube was rinsed 2 times 4 ml).

Radioactivity was measured by liquid scintillation spectrometry (Packard, Tricarb 4640) using Emulsifier-Safe (Packard) as the scintillating agent.

Specific $^3$H-paroxetine binding was defined as the difference between total binding and that remaining in the presence of 10 µM of fluoxetine.

The IC$_{50}$ were determined by transposing the percentages of inhibition onto a graph in relation to the log of the concentration of the product (6 concentrations in duplicate).

2.1.4. Products Used

F2207: batch No. 10-CTN3 Key P118
F2695: batch No. PL-I-205
F2696: batch No. PL-I-204C.

2.2. Results

The effects of F2207 and of its two enantiomers on uptake of noradrenaline and serotonin and on paroxetine binding are shown on a graph with the percentage of inhibition in relation (%) on the ordinate and the concentration (M) of F2207, F2695 and F2696 on the abscissa (data not shown). The values for the percentages of inhibition corresponding to each product concentration, tested in duplicate, are mean results of four separate experiments.

The values of the IC$_{50}$ for the three products were determined on the basis of these curves and are shown in Table 2.

TABLE 2

Inhibition of $^3$H-noradrenaline, $^3$H-serotonin uptake and $^3$H-paroxetine binding
IC$_{50}$ (M)

| Compounds | Uptake | | $^3$H-Paroxetine binding |
|---|---|---|---|
| | $^3$H-Noradrenaline | $^3$H-Serotonin | |
| F2695 | $1.5 \times 10^{-8}$ | $4.6 \times 10^{-8}$ | $6.0 \times 10^{-8}$ |
| F2207 | $3.0 \times 10^{-8}$ | $15 \times 10^{-8}$ | $13 \times 10^{-8}$ |
| F2696 | $75 \times 10^{-8}$ | $60 \times 10^{-8}$ | $70 \times 10^{-8}$ |

The three compounds were active in these three pharmacological assays, however differences were present:

in noradrenaline uptake:
F2695 was two times more active than F2207.
F2695 was 25 times more active than F2696.
in serotonin uptake:
F2695 was 3 times more active than F2207.
F2695 was 12 times more active than F2696.
in paroxetine binding:
F2695 was 2 times more active than F2207.
F2695 was 10 times more active than F2696.

The three compounds were active in these pharmacological assays with however a lesser activity for the (1R,2S) form (F2696) and the racemate (F2207). The (1S,2R) form of milnacipran (F2695) was 2 to 3 times more active than F2207.

Example No. 3

Comparative Activity of Racemic Milnacipran Hydrochloride (F2207) and of its Active (1S,2R) Enantiomer (F2695) by the Oral Route on Heart Rate and Blood Pressure in the Waking Dog 3.1. Introduction Thus study was designed to study the effects of F2207 and of F2695 a) on heart rate after a single administration by the oral route (n=28 dogs), and b) on systolic and diastolic blood pressure after repeated administration for 5 days by the oral route in dogs (n=6 dogs).

This study was conducted at equally pharmaceutically-active doses of F2207 and F2695 in female animals equipped with implants (Data Sciences International) allowing for data on heart rate and blood pressure parameters to be captured by telemetry. For every study, the animals were allocated to 3 treatment groups:

group 1 (control) treated with deionized water,
group 2 treated with F2207 at a dose of 20 mg/kg/day,
group 3 treated with F2695 at a dose of 10 mg/kg/day.

3.2. Methodology

Given the small number of simultaneously equipped animals (maximum 8), the number of recording lanes of the equipment used (8 lanes), and in order to constitute homogeneous treatment groups, the overall evaluation was performed in four studies, each study being divided into three series (treatment of each animal with each of the three products), separated by a wash-out period with reinitialization of the probes. Each series is itself performed in two phases:

a first phase during which all the animals are treated with deionized water in order to adapt them to containment and to oral treatment with stomach tubing, a second phase during which the animals receive their respective treatment (single administration for the heart rate, study Nos. 894/926/935/936; repeated administration for five days for blood pressure, study No. 894).

The overall experimental plan is described in the following table:

TABLE 3

Overall experimental plan for the telemetry study on the effects of racemic milnacipran hydrochloride (F2207) and of its active (1S, 2R) enantiomer (F2695) administered orally in conscious dogs.

| | GROUP NUMBER | | |
|---|---|---|---|
| | 1 | 2 | 3 |
| ANIMALS | | | |
| Number | 27 | 28 | 28 |
| Identification | 1-2-7-8-13-14 (study 894) | 3-4-9-10-15-16 (study 894) | 5-6-11-12-17-18 (study 894) |
| | 1-2-7-8-13-14 (study 926) | 3-4-9-10-15-16 (study 926) | 5-6-11-12-17-18 (study 926) |
| | 1-2-9-10 11-17-18-19 (study 935) | 3-4-5-12 13-20-21-22 (study 935) | 6-7-8-14 15-16-23-24 (study 935) |
| | 1-2-9-10 11-17-18-19 (study 936) | 3-4-5-12 13-20-21-22 (study 936) | 6-7-8-14 15-16-23-24 (study 936) |
| TREATMENT | | | |
| Identification | Deionized water | F2207 | F2695 |
| Dose | — | 20 mg/kg | 10 mg/kg |
| Route | | oral | |
| Volume | | 5 ml/kg | |

(n = 27 in the control group, the probe signal of animal No. 18 not having been recorded)

The effects of the various treatments on the heart rate were analyzed in the four studies after single administration. The analysis concerns the following 13 data-capture times:

prior to single administration,
every 30 minutes over 6 hours following single treatment.

The effects of the various treatments on blood pressure were analyzed in study No. 894 at the steady state, on D5, D29 and D33 (final effective day of treatment for each series). The analysis concerns the following data-capture times:
prior to treatment,
every 30 minutes over 6 hours following treatment.

3.3. Results 3.3.1. With regard to heart rate (four studies pooled), a Tukey test was performed for the individual changes in frequency, for each of the 12 post-treatment experiments, versus the pre-treatment value, as well as for the absolute heart rate values for each recording time.

The following observations were made in comparison with the control animals receiving deionized water:

\# when statistical analysis is performed on the change values (FIG. 1):
- a significant increase in heart rate from the first ½ hour following single administration of F2207 (20 mg/kg), a persistent increase up to 5.5 hours after treatment ($p \leq 0.001$ for the entire capture time, with the exception of the times 0.5 and 5.5 hours—$p \leq 0.01$—and of the time 5.0 hours—$p \leq 0.05$—after treatment),
- an increase in heart rate after the administration of F2695 which still remains less than that obtained after administration of F2207. Furthermore, this difference between the effects of F2207 and F2695 is significant ($p < 0.05$) at 1 and 4 h after administration in favor of F2695,
- an increase in heart rate which lasts for a shorter period under F2695 (1.0 to 4.5 h) than under F2207 (persists up to 5.5 h after treatment).

Figure 2:
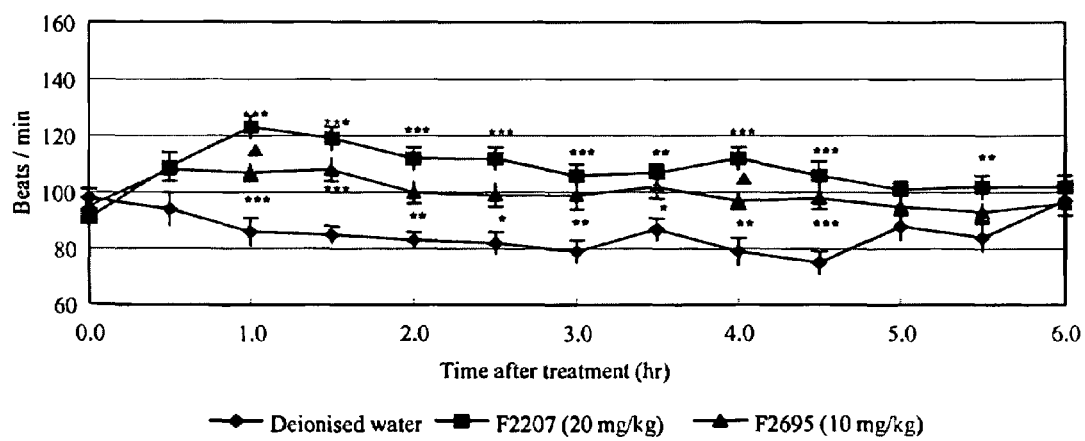
FIG. 2: Change in heart rate after single administration (absolute values).
***: $p \leq 0.001$ versus deionized water
**: $p \leq 0.01$ versus deionized water
*: $p \leq 0.05$ versus deionized water
Δ: $p \leq 0.05$ versus F2207

\# when statistical analysis is performed on absolute heart rate values, this same study demonstrates (FIG. 2):
- a significant increase in heart rate from the first hour following single administration of F2207 (20 mg/kg), a persistent increase up to 5.5 hours after treatment ($p \leq 0.001$ for the entire capture time of 1.0 to 4.5 hours, with the exception of the time 3.5 hours—$p \leq 0.01$; and $p \leq 0.01$ for the capture time 5.5 hours after treatment),
- an increase in heart rate after the administration of F2695 which still remains less than that obtained after administration of F2207. Furthermore, this difference between the effects of F2207 and F2695 is significant ($p < 0.05$) at 1 and 4 h after administration in favor of F2695,
- an increase in heart rate which lasts for a shorter period under F2695 (1.0 to 4.5 h) than under F2207 (persists up to 5.5 h after treatment).

Figure 3:
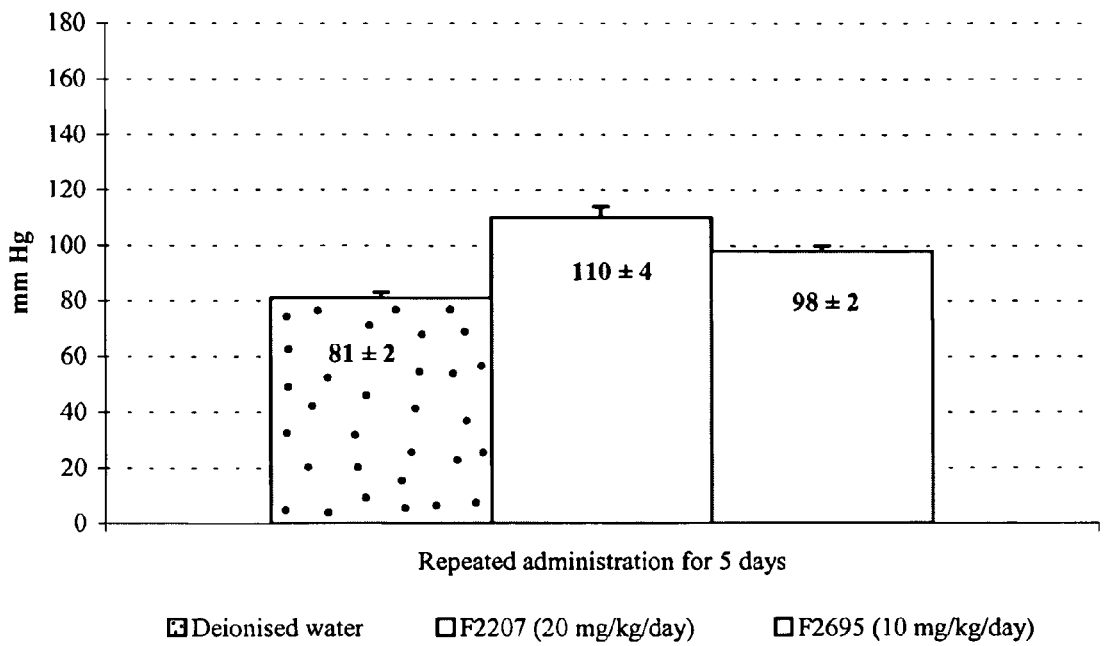
FIG. 3: Effects of various treatments on mean values of diastolic blood pressure (mean values over 6 hours following the last intake, after 5 consecutive days of treatment).
Figure 4:
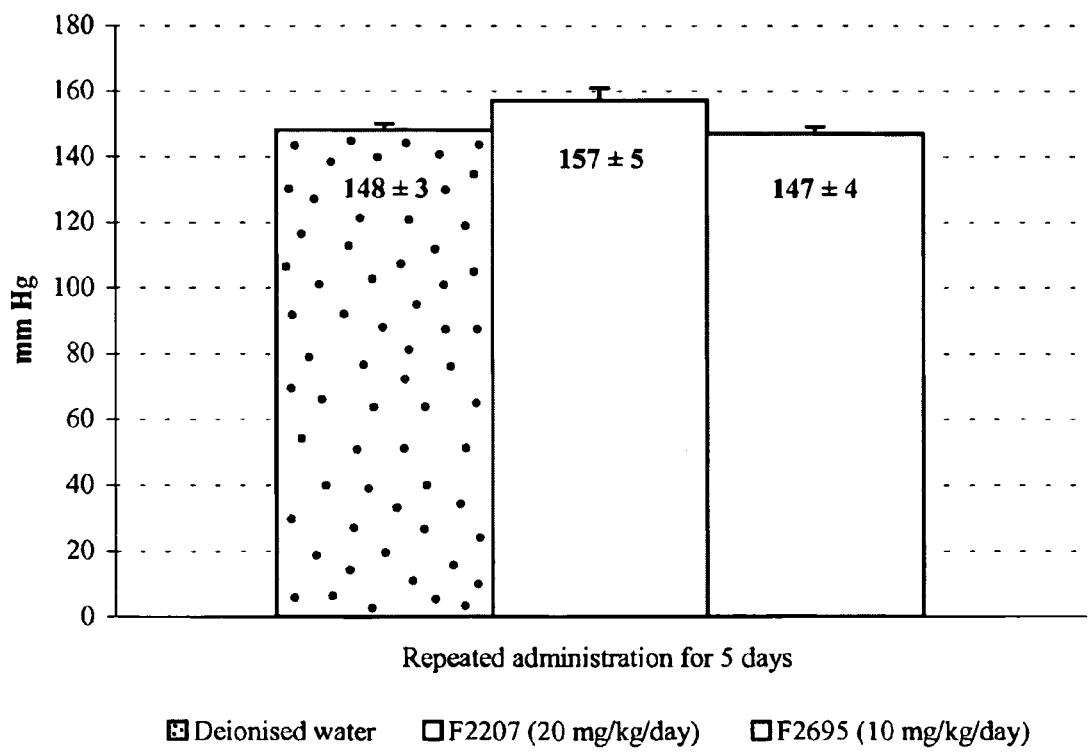
FIG. 4: Effects of various treatments on mean values of systolic blood pressure (mean values over 6 hours following the last intake, after 5 consecutive days of treatment).

3.3.2. With regard to blood pressure (one study of repeated administration), one mean value for diastolic blood pressure (FIG. 3 and Table 4), as well as one mean value for systolic blood pressure (FIG. 4 and Table 5) were calculated for each dog and for the 6 hours following the final treatment, after 5 consecutive days of administration. These mean blood pressure values were analyzed by ANOVA followed by a Tukey test when ANOVA permitted such a test (data not shown).

The following were observed:
- a significant increase ($p \leq 0.001$) in diastolic blood pressure after repeated administration of F2207 for 5 days (20 mg/kg/day) or of F2695 (10 mg/kg/day) compared to treatment with deionized water,
- a significant difference ($p \leq 0.05$) in the mean diastolic blood pressure value after repeated administration of F2207 (20 mg/kg/day) for 5 days compared to the mean diastolic blood pressure value after repeated administration of F2695 (10 mg/kg/day),
- no significant effect on systolic blood pressure; it should be noted however that the values for sBP after repeated administration of F2695 for 5 days are close to the values for sBP following treatment with deionized water.

Individual diastolic and systolic blood pressure data are shown in Tables 4 and 5 respectively.

TABLE 4

Individual diastolic blood pressure data
DIASTOLIC BLOOD PRESSURE (dBP expressed in mmHg)
Individual data after repeated administration for 5 consecutive days

| | GROUP | | | | | | | | | | | | | | |
|---|---|---|---|---|---|---|---|---|---|---|---|---|---|---|---|
| | 1 | | | | | | | | 2 | | | | | | |
| | TREATMENT | | | | | | | | | | | | | | |
| | VEHICLE | | | | | | | | F2207 (20 mg/kg/d) | | | | | | |
| | Animal N° | | | | | | | | | | | | | | |
| | 1 | 2 | 7 | 8 | 13 | 14 | M | SEM | 3 | 4 | 9 | 10 | 15 | 16 | M | SEM |
| Time before treatment | 79 | 77 | 73 | 77 | 101 | 76 | 81 | 4 | 112 | 89 | 93 | 88 | 86 | 91 | 93 | 4 |
| Time after treatment(h) | | | | | | | | | | | | | | | | |
| 0.50 | 84 | 76 | 70 | 63 | 80 | 70 | 74 | 3 | 103 | 106 | 96 | 92 | 88 | 87 | 95 | 3 |
| 1.00 | 82 | 84 | 77 | 72 | 72 | 76 | 77 | 2 | 130 | 117 | 113 | 113 | 90 | 106 | 112 | 5 |
| 1.50 | 102 | 81 | 79 | 75 | 82 | 68 | 81 | 5 | 131 | 127 | 137 | 96 | 100 | 91 | 114 | 8 |
| 2.00 | 83 | 75 | 71 | 98 | 77 | 75 | 80 | 4 | 123 | 113 | 99 | 88 | 107 | 109 | 107 | 5 |
| 2.50 | 85 | 75 | 75 | 84 | 85 | 79 | 81 | 2 | 137 | 111 | 116 | 101 | 115 | 107 | 115 | 5 |
| 3.00 | 91 | 95 | 99 | 85 | 79 | 84 | 89 | 3 | 121 | 118 | 112 | 116 | 106 | 92 | 111 | 4 |
| 3.50 | 83 | 72 | 78 | 73 | 77 | 65 | 75 | 3 | 120 | 106 | 133 | 116 | 103 | 103 | 114 | 5 |
| 4.00 | 81 | 79 | 75 | 77 | 82 | 68 | 77 | 2 | 133 | 114 | 105 | 111 | 110 | 103 | 113 | 4 |
| 4.50 | 82 | 76 | 91 | 84 | 113 | 85 | 89 | 5 | 135 | 110 | 126 | 109 | 104 | 108 | 115 | 5 |
| 5.00 | 97 | 79 | 67 | 95 | 81 | 82 | 84 | 5 | 116 | 120 | 98 | 97 | 97 | 105 | 106 | 4 |

TABLE 4-continued

Individual diastolic blood pressure data
DIASTOLIC BLOOD PRESSURE (dBP expressed in mmHg)
Individual data after repeated administration for 5 consecutive days

| | | | | | | | | | | | | | | | | |
|---|---|---|---|---|---|---|---|---|---|---|---|---|---|---|---|---|
| 5.50 | 94 | 80 | 70 | ND | 85 | 82 | 82 | 4 | 103 | 107 | 115 | 106 | 92 | 93 | 103 | 4 |
| 6.00 | 83 | 74 | 82 | 82 | 78 | 77 | 79 | 1 | 115 | 133 | 120 | 104 | 103 | 104 | 113 | 5 |
| Mean dBP after treatment | 87 | 79 | 78 | 81 | 83 | 76 | 81 | 2 | 122 | 115 | 114 | 104 | 101 | 101 | 110 | 4 |

| | GROUP 3 |
|---|---|
| | TREATMENT |
| | F2695 (10 mg/kg/d) |
| | Animal N° |

| | 5 | 6 | 11 | 12 | 17 | 18 | M | SEM |
|---|---|---|---|---|---|---|---|---|
| Time before treatment | 73 | 89 | 80 | 71 | 76 | 78 | 78 | 3 |
| Time after treatment(h) | | | | | | | | |
| 0.50 | 91 | 91 | 99 | 90 | 108 | 85 | 94 | 3 |
| 1.00 | 112 | 96 | 75 | 97 | 87 | 96 | 94 | 5 |
| 1.50 | 109 | 83 | 88 | 97 | 87 | 112 | 96 | 5 |
| 2.00 | 115 | 88 | 93 | 95 | 84 | 109 | 97 | 5 |
| 2.50 | 111 | 88 | 97 | 89 | 92 | 107 | 97 | 4 |
| 3.00 | 104 | 91 | 96 | 96 | 100 | 106 | 99 | 2 |
| 3.50 | 96 | 106 | 94 | 107 | 77 | 103 | 97 | 5 |
| 4.00 | 125 | 91 | 99 | 108 | 80 | 109 | 102 | 6 |
| 4.50 | 103 | 104 | 92 | 100 | 85 | 108 | 99 | 3 |
| 5.00 | 126 | 100 | 92 | 95 | 110 | 102 | 104 | 5 |
| 5.50 | 88 | 86 | 105 | 98 | 89 | 99 | 94 | 3 |
| 6.00 | 101 | 113 | 98 | 105 | 109 | 108 | 106 | 2 |
| Mean dBP after treatment | 107 | 95 | 94 | 98 | 92 | 104 | 98 | 2 |

ND: not determined

TABLE 5

Individual systolic blood pressure data
SYSTOLIC BLOOD PRESSURE (sBP expressed in mmHg)
Individual data after administration for 5 consecutive days

| | GROUP 1 | | | | | | | | GROUP 2 | | | | | | | |
|---|---|---|---|---|---|---|---|---|---|---|---|---|---|---|---|---|
| | TREATMENT | | | | | | | | | | | | | | | |
| | VEHICLE | | | | | | | | F2207 (20 mg/kg/d) | | | | | | | |
| | Animal N° | | | | | | | | | | | | | | | |
| | 1 | 2 | 7 | 8 | 13 | 14 | M | SEM | 3 | 4 | 9 | 10 | 15 | 16 | M | SEM |
| Time before treatment | 139 | 141 | 120 | 157 | 172 | 138 | 145 | 7 | 188 | 164 | 176 | 149 | 130 | 169 | 163 | 8 |
| Time after treatment(h) | | | | | | | | | | | | | | | | |
| 0.50 | 135 | 132 | 119 | 131 | 149 | 138 | 134 | 4 | 158 | 154 | 152 | 128 | 126 | 129 | 141 | 6 |
| 1.00 | 134 | 158 | 129 | 144 | 141 | 143 | 142 | 4 | 180 | 167 | 157 | 150 | 126 | 130 | 152 | 9 |
| 1.50 | 158 | 151 | 145 | 150 | 153 | 137 | 149 | 3 | 186 | 181 | 189 | 129 | 136 | 138 | 160 | 12 |
| 2.00 | 138 | 136 | 145 | 173 | 151 | 144 | 148 | 5 | 171 | 160 | 146 | 122 | 140 | 163 | 150 | 7 |
| 2.50 | 142 | 143 | 145 | 159 | 160 | 148 | 150 | 3 | 195 | 168 | 168 | 144 | 153 | 161 | 165 | 7 |
| 3.00 | 149 | 167 | 162 | 163 | 150 | 154 | 158 | 3 | 173 | 177 | 164 | 157 | 141 | 146 | 160 | 6 |
| 3.50 | 135 | 129 | 149 | 154 | 153 | 137 | 143 | 4 | 165 | 153 | 184 | 167 | 139 | 155 | 161 | 6 |
| 4.00 | 142 | 143 | 149 | 166 | 164 | 144 | 151 | 4 | 180 | 157 | 151 | 154 | 150 | 153 | 158 | 5 |
| 4.50 | 137 | 140 | 159 | 170 | 190 | 152 | 158 | 8 | 184 | 161 | 180 | 155 | 145 | 168 | 166 | 6 |
| 5.00 | 150 | 146 | 127 | 177 | 160 | 145 | 151 | 7 | 161 | 171 | 146 | 141 | 139 | 166 | 154 | 6 |
| 5.50 | 153 | 149 | 132 | ND | 148 | 144 | 145 | 4 | 151 | 154 | 173 | 152 | 132 | 155 | 153 | 5 |

TABLE 5-continued

Individual systolic blood pressure data
SYSTOLIC BLOOD PRESSURE (sBP expressed in mmHg)
Individual data after administration for 5 consecutive days

| | | | | | | | | | | | | | | | |
|---|---|---|---|---|---|---|---|---|---|---|---|---|---|---|---|
| 6.00 | 146 | 144 | 151 | 176 | 146 | 143 | 151 | 5 | 158 | 192 | 171 | 154 | 148 | 172 | 166 | 7 |
| Means BP after treatment | 143 | 145 | 143 | 160 | 155 | 144 | 148 | 3 | 172 | 166 | 165 | 146 | 140 | 153 | 157 | 5 |

GROUP 3
TREATMENT
F2695 (10 mg/kg/d)
Animal N°

| | 5 | 6 | 11 | 12 | 17 | 18 | M | SEM |
|---|---|---|---|---|---|---|---|---|
| Time before treatment | 136 | 141 | 138 | 130 | 134 | 149 | 138 | 3 |
| Time after treatment(h) | | | | | | | | |
| 0.50 | 135 | 129 | 140 | 135 | 160 | 139 | 140 | 4 |
| 1.00 | 159 | 135 | 124 | 148 | 131 | 143 | 140 | 5 |
| 1.50 | 164 | 119 | 138 | 158 | 127 | 156 | 144 | 8 |
| 2.00 | 168 | 125 | 135 | 141 | 127 | 156 | 142 | 7 |
| 2.50 | 165 | 124 | 142 | 141 | 134 | 154 | 143 | 6 |
| 3.00 | 156 | 131 | 145 | 144 | 151 | 157 | 147 | 4 |
| 3.50 | 146 | 147 | 141 | 169 | 123 | 156 | 147 | 6 |
| 4.00 | 180 | 132 | 145 | 160 | 124 | 164 | 151 | 9 |
| 4.50 | 158 | 151 | 138 | 163 | 131 | 163 | 151 | 5 |
| 5.00 | 182 | 144 | 137 | 150 | 162 | 158 | 156 | 6 |
| 5.50 | 142 | 127 | 152 | 153 | 141 | 153 | 145 | 4 |
| 6.00 | 156 | 170 | 148 | 159 | 160 | 166 | 160 | 3 |
| Means BP after treatment | 159 | 136 | 140 | 152 | 139 | 155 | 147 | 4 |

ND: not determined 3.4. Conclusion

Under the experimental conditions of the present evaluation carried out in four successive studies by oral administration in the waking dog equipped with a telemetric device:

- on single administration and compared to the control group (n=28), the increase in heart rate was clearly significant and lasting with F2207 at a dose of 20 mg/kg/day; it is statistically and clinically reduced and more fleeting with F2695 at the equally pharmacologically-active dose of 10 mg/kg/day.
- F2695, at a dose of 10 mg/kg/day, did not induce any statistically significant change in mean systolic blood pressure over the 6 hours following the final treatment, at the steady state after repeated administration for 5 days,
- a statistically significant difference was evidenced in mean diastolic blood pressure over the 6 hours following the final treatment, at the steady state after repeated administration for 5 days, between the active F2695 enantiomer (98±2 mm Hg) and the F2207 racemic at equally pharmaceutically-active doses (110±4 mm Hg).

These differences clearly demonstrated greater cardiovascular tolerability of the active F2695 enantiomer.

Example 4

Genomic Test of Predictive Toxicology In Vitro 4.1. Materials and Methods

The F2695 and F2696 compounds, enantiomers of the racemic molecule F2207, as well as clomipramine, a reference product, (coded C218 in the study) were assessed in the present study. The two enantiomers, F2695 and F2696, were first assessed in a preliminary cytotoxicity test (MTT assay) on primary rat hepatocytes, in order to select the three concentrations to be used in the final test.

After treatment of the primary rat hepatocytes in culture, the RNA was extracted in order to generate labeled complementary-DNA probes which were then hybridized on a membrane containing 682 alternatively-spliced fragments specific to cell stress. A Toxicity Index was obtained for each of the products by comparing the hybridization profile of the treated cells with that of the untreated cells.

4.1.1. Purpose and Aim of the Study

Safe-Hit is a genomic test for predictive toxicopharmacology that is sensitive, robust, reliable, rapid and sure, enabling products to be compared and ranked on the basis of optimized assessment of their toxic potential.

Safe-Hit uses technology, the property of EXONHIT (DATAS™: Differential Analysis of Transcripts with Alternative Splicing), that permits isolation and, consequently, cloning of splicing events that result from a given biological state, in comparison with a control condition. This allows mRNA isoforms, differentially expressed depending on the biological conditions, to be isolated.

Safe-Hit allows molecules within a chemical series to be ranked according to a Toxic Index, determined after the following basic steps (systematically performed in duplicate for each product):

- treatment of the cell lines with the various products at three different concentrations, deduced from a preliminary cytotoxicology test (MTT assay): a reference concentration corresponding to 80% cell viability, a concentration 10-fold higher—when possible—and a concentration 10-fold lower, preparation of total RNA and of the corresponding radiolabeled cDNA probes, hybridization of the cDNA probes: Safe-Hit macro-array containing 682 independent clones, corresponding to alterations in gene splicing induced by overexpression of WTp53 (p53 is the most ubiquitous "mediator" of cell stress, chosen from the development of this methodology), acquisition and determination of the Toxicity Index.

4.1.2. Cells

The cells used in the study (preliminary MTT assay of cytotoxicity and the main test) are cryopreserved hepatocytes from Sprague-Dawley rats in primary culture (batches Hep 184005 and Hep 184006—Biopredic), cultured under standard conditions.

4.1.2.1 Culture Medium thawing medium: Leibovitz 15 medium with glutamax 1, to which were added 100 IU/ml of penicillin, 100 µg/ml of streptomycin and 0.6 M of glucose (batch MIL 210009—Biopredic), seeding medium: Williams E medium with glutamax 1, to which were added 100 IU/ml of penicillin, 100 µg/ml of streptomycin, 4 µg/ml of bovine insulin and 10% v/v fetal calf serum (batch MIL 260005)—Biopredic), incubation medium: Williams E medium with glutamax 1, to which were added 100 IU/ml of penicillin, 100 µg/ml of streptomycin, 4 µg/ml of bovine insulin and 50 µM of hydrocortisone hemisuccinate (batch MIL 260009-260007—Biopredic).

4.1.2.2 Culture Conditions

37° C., CO2 atmosphere (5%), relative humidity (95%).

4.1.2.3 Culture Procedure

|  | Cell toxicity test | Main study |
| --- | --- | --- |
|  | Cells were seeded on the day of treatment. | |
| Seeding density | 35 000 cells/well (96 wells per plate) | 1.5 million cells per 30 mm plate |
| Medium volume | 0.1 ml | 3 ml |

4.1.3. Cytoxicity Test

The cytoxicity test (MTT assay) detects live cells by use of a calorimetric reaction that reveals the integrity of cell respiration implying activity of the mitochondria. MTT (3-[4,5-dimethylthiazol-2-yl]-2,5-diphenyltetrazolium bromide), soluble in water, is transformed by splitting, under the effect of a mitochondrial enzyme in live cells, into insoluble purple formazan. Formazan is solubilized in an organic solvent and the solution obtained can be measured by spectrophotometry. The absorbance measured is proportional to the number of surviving cells.

The cells are put into contact with the product to be tested at 5 different concentrations (0–1–10–25–50 and 100 µM) for 16 hours.

After this period of exposure, an MTT solution (0.5 mg/ml in the incubation medium of the primary hepatocytes) is added for 3 hours. After solubilization of the formazan crystals, the multi-well plates are read with a spectrophotometer at 500 nm in order to determine the percentage of cell viability.

4.1.4 Main Genomic Pharmacotoxicology Test

The main study is performed in duplicate, using seeded cultures exposed to each product in order to enhance consistency between the experiments and to validate the results obtained.

4.1.4.1 Cell Seeding and Treatment

The cells are seeded and cultured for 16 hours with each product, at the three concentrations chosen on the basis of the preliminary MTT assay; two controls (untreated cells and solvent alone) are added to the series.

4.1.4.2 Total RNA Extraction and Assay

After treatment, the RNA is extracted and analyzed as follows:

collection of cells and centrifugation, extraction performed with ready-to-use phenol reagent (Trizol—batches 1106266 and 1121067—Invitrogen) according to the manufacturer's protocol, solubilization of the RNA in water, RNA assay by spectrophotometry (optical density measured at 260, 280 and 300 nm), verification of the quality of the RNA using Agilent.

4.1.4.3 Preparation of the cDNA Probes

The cDNA probes are prepared by reverse radioactive transcription (alpha dATP $^{33}$p—Amersham). The radioactive cDNA is quantified (Instant Imager—Packard) to ensure that the probes are active.

4.1.4.4 Hybridization on the Safe-Hit Membrane

The 682 DATAS clones (alternately spliced patterns) are placed in duplicate on the Safe-Hit membranes, made of precut nylon (Q-BIOgene), with the aid of a Q-Pix apparatus (GENETIX). The DNA probes are hybridized on the membranes overnight and the membranes are washed.

4.1.4.5. Preparation of the cDNA:

matrix: 5 µg of total RNA (for each treatment series and for each concentration), primer: 100 ng of oligo-dTV oligonucleotide, for the 1 st and 2nd hybridizations in rats (batch 12.00, Invitrogen), main mixture:

10 µl of First Strand 5× Premier buffer (batch 1131226—Invitrogen)

1 µl of dCTP+dGTP+dTTP 20 mM (batch 1105201—Invitrogen)

1 µM of ATP 120 µM (batch 1105201—Invitrogen)

5 µl of Dithiothreitol (DTT) 0.1 M (batch 133609—Invitrogen)

1 µl of Out 40 U RNase (batch 1113345—Invitrogen)

5 µl of $^{33}$p dATP 3 000 Ci/mmol 10 m Ci/µl (batch B0239—Amersham)

4 µl of Superscript II (batch 1137806—Invitrogen)

1 µl of glycogen (batch 1129328—Invitrogen)

Procedure:

Incubate the RNA and the oligo-dTV at 70° C. for 10 minutes and then place it on ice. Add 27 µl of MasterMix and incubate at 43° C. for 1 h then at 50° C. for 15 minutes. Add 20 µl of water, then 20 µl of EDTA 50 mM, then 4 µL of NaOH 10N. Incubate for 20 minutes at 65° C. then place on ice.

Quantification: Instant Imager, Packard: 1 µl of reaction mixture, add 8 µl of acetic acid, 100 µl of isopropanol and 1 µl of glycogen (20 µg/µl). Incubate at −20° C. for 20 minutes, centrifuge for 20 minutes at 13 000 rpm at 4° C. Reconstitute as a suspension in 200 µl of water, quantification: Instant Imager, Packard: 1 µl of reaction mixture.

| Media and buffers | |
|---|---|
| Common solutions: | Washing buffer 1: |
| 20X SSC (Invitrogen)<br>50X Denhardt's<br>50% (w/v) Dextran Sulfate (ICN)<br>20% SDS (v/v)(Quantum biotech.)<br>10 mg/ml DNA from salmon sperm<br>(Q-Biogene) | 2X SSC |
| Prehybridization buffer: | Washing buffer 2: |
| 6X SSC<br>10X Denhardt's<br>10% Dextran Sulfate<br>0.5% SDS<br>H$_2$O | 2X SSC<br>0.1% SDS |
| Hybridization buffer: | Washing buffer 3: |
| 5X SSC<br>5X Denhardt's<br>0.1% SDS<br>H$_2$O | 0.5X SSC<br>0.1% SDS |
| | Washing buffer 4: |
| | 1X SSC<br>0.1% SDS |

Prehybridization:
Aliquot 5 ml of prehybridization buffer in the hybridization tubes, add the corresponding volume of salmon-sperm DNA for a final concentration of 100 µg/ml, soak the membranes in 5×SSC, place the membrane in the hybridization tube and prehybridize for 2 hours at 65° C.

Hybridization:
Remove the prehybridization buffer and rinse with 10–20 ml of 5×SSC, remove the 5×SSC, replace with 5 ml of buffer+salmon-sperm DNA, denature the RT probes for 5 min at 95° C., then place on ice for 1 minute, centrifuge to reconstitute, then recover the appropriate volume of denatured RT probes in the tube (100 000 to 200 000 cpm/ml), incubate overnight at 55° C.

Washing:
Rinse the membranes with 10–20 ml of washing buffer 1, remove the buffer and replace it with 50 ml of washing buffer 2, incubate for 30 min at 35° C., then remove and replace while washing with buffer 4, incubate for 30 min at 55° C., then pour off the final washing buffer, remove the membranes from the tubes, place them on a cassette and allow acquisition to continue for 3 hours.

4.1.4.6 Acquisition and Analysis of the Image

The membranes are placed on a screen (FX Imaging ScreenK—Bio-rad) for 3 hours. The film is then read using a Personal Molecular Imager FX (Bio-rad). The image is analyzed using the Safe-Hit Reader Software (COSE).

4.1.4.7 Calculation of the Toxicity Index

All the data are transferred to an automatic calculation program that normalizes the various membranes and calculates a Toxicity Index, equal to the sum of the number of up- and down-regulated genes for a given compound at a given concentration, in comparison with the results of the untreated controls. The results of the two Safe-Hit analyses are then compared and combined to assess the potential toxicity of the various compounds tested. Two parameters that can be modified by the user are involved in the calculation of the Toxicity Index:

Background Threshold (BT) smoothes out weak signals, close to background noise and not attributable to significant gene expression. This therefore determines the threshold of detection;

Induction Factor (IF) is determined as the multiplication factor, versus the control samples, for the clones to be up- or down-regulated. The value of this parameter is usually 2 or less than 2 in order to obtain relevant results. Progressively increasing the IF value selects those clones that are more and more strongly up- or down-regulated.

Figure 5:
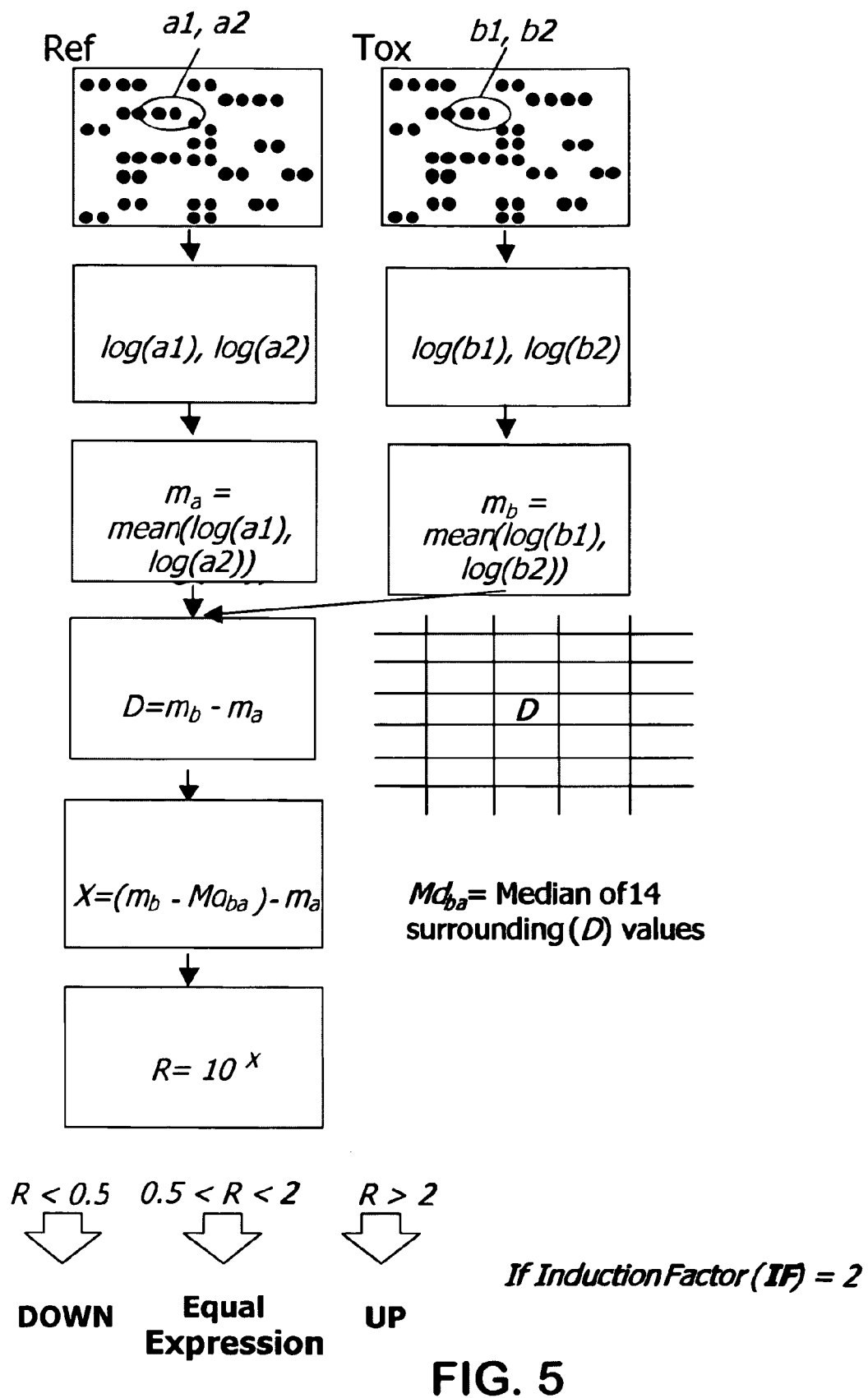
FIG. 5: Schematic representation of the method of calculation of the Toxicity Index. The Toxicity Index is the sum of all up- and down-regulated genes (in relation to the Induction Factor defined by the user)

The procedure for calculating the Toxicity Index was developed by comparing the reference profiles (R: untreated cells) with an experimental profile (E) and goes through the following steps (see FIG. 5 for a schematic overview of the procedure):

transformation of all the values obtained into log values, calculation of the mean log value for each of the duplicate assays ($M_{iR}$ and $M_{iE}$), creation of a matrix with $M_{iR}$-$M_{iE}$ for all the signals (=$D_i$), normalization of the individual $M_{iE}$ values by subtracting from $M_{iE}$ the median of the 14 proximal values of $D_i$(=$NM_{iE}$), comparison of the normalized values with the reference values ($C_i$=$NM_{iE}$–$M_{iR}$), exponential transformation of $C_i$(=$F_i$), comparison of $F_i$ with the Induction Factor chosen by the user:

if $F_i$>IF, the gene is considered to be up-regulated, if $1/IF<F_i<IF$, the gene is considered to be without change, if $F_i$<1/IF, the gene is considered to be down-regulated.

4.2. Results of the MTT Assay

These assays were performed in triplicate on primary rat hepatocytes exposed for 16 hours.

Clomipramine, referred to as C218, showed marked toxicity at 100 µM since no cell viability was observed after exposure of the cells for 16 hours. Conversely, no toxicity was observed at 25 µM. At 50 µM, cell viability greater than 80% is entirely compatible with a genomic pharmacotoxicology study. The F2695 and F2696 compounds show no cytotoxicity in this assay, even at a concentration of 100 µM.

To perform the genomic pharmacotoxicological assessments, 3 concentrations of the same compound are used: the concentration which allows for 80% cell viability (C) to be obtained, as well as concentrations corresponding to (C)×10 and to (C)/10.

Figure 6A:
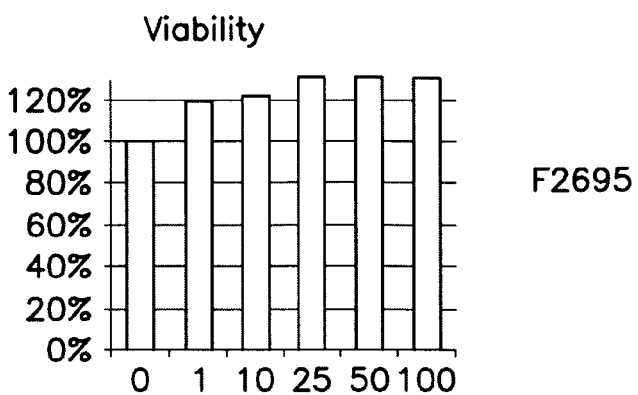
FIGS. 6a, 6b, 6c: MTT assay on primary rat hepatocytes. The concentrations are expressed in μM.
Figure 6B:
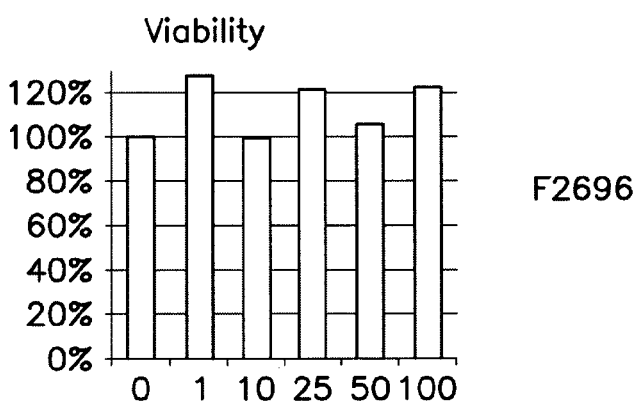
Figure 6C:
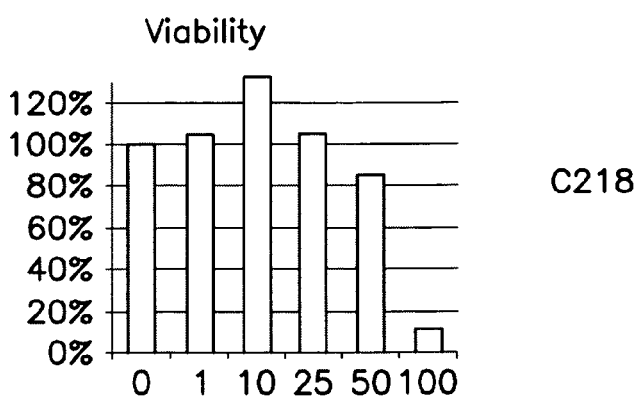

In order to compare the capacity of F2695 and F2696 to yield a score in the assay performed, the same concentrations were used in each test: 1 µM, 10 µM and 100 µM. Concentrations of 1 µM, 10 µM and 50 µM were used for clomipramine. See FIGS. 6a, 6b and 6c.

4.3 Results on Primary Rat Hepatocytes

Toxicity Indices (IT) were determined as described above. Only those clones which were found to be altered in relation to the control were taken into account in the two independent experiments, taking into consideration only those clones whose signal was two times higher than the background threshold (BT). Two separate analyses were performed using two levels of differentiation (Induction Factor—IF) in relation to the untreated controls:
a factor of at least 1.7 in relation to the untreated controls. This factor of 1.7 times represents the weakest value that allows an index not to be obtained in relation to the two untreated controls.

a factor of at least 2 in relation to the untreated controls. This factor of 2 times allows the most robust signals to be taken into account.

4.3.1. Induction Factor of 1.7 in Relation to the Untreated Controls (Table 6)

TABLE 6

| | | | \multicolumn{9}{c|}{Up- and down-regulated clones with primary rat hepatocytes (Induction Factor = 1.7 times)} |
|---|---|---|---|---|---|---|---|---|---|---|---|---|
| | | | F2695-1 µM | F2695-10 µM | F2695-100 µM | F2696-1 µM | F2696-10 µM | F2696-100 µM | C 218-1 µM | C 218-10 µM | C 218-100 µM | |
| Up | >1.7 | Up | | | 1 | | | 15 | 2 | 2 | 13 | |
| Down | <0.588 | Down | | | 1 | 2 | 5 | 7 | 7 | 13 | 15 | |
| | | TI | | | 2 | 2 | 5 | 22 | 9 | 15 | 28 | |
| Pos | No. U | No. D | | | | | | | | | | Gene |
| A09 | 3 | | | | | | | | 2.90 | 2.23 | 2.14 | H. sapiens mitochondrion, 12S |
| A20 | | 1 | | | | | | 0.56 | | | | H. sapiens initiation factor elF-5A gene |
| B20 | | 2 | | | | | | | | 0.14 | 0.27 | H. sapiens chromosome 19, BAC CIT-B-191n6 |
| B22 | | 2 | | | | | | | | 0.17 | 0.32 | H. sapiens Genomic sequence from 17 |
| C01 | 4 | | | | | | | 3.20 | 1.93 | 1.82 | 1.91 | H. sapiens mitochondrion, 16S |
| E01 | 1 | | | | | | | | | | 1.73 | H. sapiens mRNA for lipocortin II |
| E05 | | 2 | | | | | | | | 0.22 | 0.35 | H. sapiens DNA sequence from clone 740A11 on chromosome Xq22.2–23. Contains part of the COL4A5 gene for Collagen Alpha 5 (IV) Chain Precursor. Contains GSS1, complete sequence |
| E11 | 1 | | | | | | | 2.12 | | | | H. sapiens chlordecone reductase homolog liver, mRNA |
| E19 | 1 | | | | | | | | | | 1.72 | H. sapiens mitochondrion, cytochrome c oxidase subunit 1 |
| E21 | | 2 | | | | | | | | 0.56 | 0.58 | H. sapiens ribosomal protein S14 gene |
| F24 | | 1 | | | | | | | | | 0.52 | H. sapiens LIM homeobox protein cofactor (CLIM-1) mRNA |
| G01 | 1 | | | | | | | | | | 2.04 | H. sapiens estrogen receptor-related protein (variant ER from breast cancer) mRNA |
| G05 | 1 | | | | | | | | | | 2.02 | H. sapiens mitochondrion, cytochrome c oxidase subunit 1 |
| G09 | 2 | | | | | | | 2.09 | | | 1.76 | H. sapiens mitochondrion, cytochrome b |
| I01 | 1 | | | | | | | 2.05 | | | | H. sapiens mitochondrion, cytochrome c oxidase subunit 1 |
| I18 | 2 | | | | | | | 2.38 | | | 1.88 | H. sapiens 18S rRNA gene |
| L01 | 1 | | | | | | | 2.05 | | | | H. sapiens divalent cation tolerant protein CUTA mRNA |
| L22 | 1 | | | | | | | 1.78 | | | | H. sapiens mRNA for Lon protease-like protein |
| L23 | 1 | | | | | | | | | | 1.75 | H. sapiens cDNA NIH_MGC_16 clone IMAGE: 3350241 5', mRNA sequence |
| M07 | 2 | | | | | | | 2.25 | | | 1.75 | H. sapiens mitochondrion, cytochrome c oxidase subunit 1 |
| M12 | | 3 | | | | | | 0.21 | | 0.16 | 0.39 | H. sapiens mRNA; cDNA DKFZp564C1563 |
| M23 | 1 | | | | | | | 1.95 | | | | Sequence 21 from U.S. Pat. No. 5851764 |
| P05 | 1 | | | | | | | 1.78 | | | | H. sapiens PAC clone DJ404K21 from Xq23 |

TABLE 6-continued

Up- and down-regulated clones with primary rat hepatocytes (Induction Factor = 1.7 times)

| | | | | | | | | | |
|---|---|---|---|---|---|---|---|---|---|
| Q11 | 2 | | 1.81 | | | | | 1.92 | unk |
| Q24 | 1 | | | | 1.77 | | | | H. sapiens 28S ribosomal RNA gene |
| S01 | 1 | | | | | | | 2.98 | Mus muculus TCR beta locus |
| T08 | 6 | | 0.50 | 0.22 | 0.20 | 0.35 | 0.14 | 0.22 | H. sapiens mRNA for KIAA1185 protein |
| U04 | 6 | | 0.57 | 0.26 | 0.19 | 0.48 | 0.22 | 0.37 | H. sapiens translation initiation factor eIF-2alpha mRNA |
| V22 | | | | | | | | | H. sapiens mRNA for elongation factor 1-alpha (clone CEF4) |
| W17 | 1 | | | | 2.96 | | | | H. sapiens mitochondrion, hypoxia inducible gene-14 |
| X02 | 5 | | | 0.29 | 0.20 | 0.36 | 0.24 | 0.31 | unk |
| X05 | 2 | | | | | | 0.15 | 0.24 | H. sapiens microsomal epoxide hydrolase (EPHX) gene |
| X06 | 5 | | | 0.2 | 0.16 | 0.23 | 0.15 | 0.23 | H. sapiens Genomic sequence from 9q34 |
| X23 | 1 | | | | 1.92 | | | | unk |
| Y17 | 1 | | | | 2.65 | | | | H. sapiens 28S ribosomal RNA gene |
| Z13 | 3 | | | | | 0.34 | 0.29 | 0.27 | unk |
| Z20 | 1 | | | | | | | 0.57 | Homo sapiens cDNA wc44h09, x1 NCI_CGAP_Pr28 clone IMAGE: 2321537 3' similar to SW: RB24_Mouse P35290 RAS_RELATED PROTEIN RAB-24;, mRNA sequence |
| AA11 | 3 | | | | | 0.38 | 0.27 | 0.31 | H. sapiens Repeat sequence AluJb fragment inserted into a cDNA coding for an unknown protein |
| AA13 | 1 | | | | | | | 1.79 | H. sapiens 18S rRNA gene |
| AC13 | 5 | | | 0.22 | 0.16 | 0.28 | 0.16 | 0.28 | H. sapiens 7S RNA L gene |

The following Toxicity Indices were obtained:

| F2695 | Toxicity Index |
|---|---|
| 1 µM | 0 |
| 10 µM | 0 |
| 100 µM | 17 |

| F2696 | Toxicity Index |
|---|---|
| 1 µM | 2 |
| 10 µM | 5 |
| 100 µM | 22 |

| C218 | Toxicity Index |
|---|---|
| 1 µM | 9 |
| 10 µM | 15 |
| 50 µM | 28 |

The following ranking could thus be established, from the most to the least toxic:

C218 (clomipramine)>F2696>>>F2695.

Clomipramine, the reference molecule, coded C218 in the present study, showed an increasing number of signatures with relation to the concentrations tested: respectively 9, 15 and 28 signatures at concentrations of 1, 10 and 50 µM (maximal concentration defined in the preliminary cytotoxicity test). As one might logically expect, all the signatures that occurred at low and moderate concentrations are also found at higher concentrations.

At concentrations of 1 and 10 µM, F2695 did not induce any of the 682 potential signatures of stress tested in the present study. At the highest concentration, 100 µM, only two signatures were detected, one of which was common to C218, but whose signification was unknown.

F2696 showed an increasing number of signatures in relation to the concentrations tested: 2, 5 and 22 signatures respectively at concentrations of 1, 10 and 100 µM. All of the signatures that occurred at the low and medium concentrations were detected at the higher concentrations. None of the 22 signatures was shared with F2695. Conversely, the signatures that appeared at the low and medium concentrations (5 including the 2 which were present at the low concentration) were among the 5 that formed part of the 9 signatures detected with clomipramine starting with the low dose, 1 µM. At the high concentration, 100 µM, 10 of the 26 signatures of F2696 were detected among the 28 signatures identified with clomipramine at 50 µM.

From the qualitative standpoint, the impact of F2696 and of clomipramine on mitochondrial transcripts, in particular on Cox1 and on cytochrome b, should be stressed. These signatures are not present with F2695 (G05/G09/I01 positions).

4.3.2. Induction Factor of 2 in Relation to Untreated Controls (Table 7)

TABLE 7

Up- and down-regulated clones with primary rat hepatocytes (Induction Factor = 2 times)

| | | | F2695-1 μM | F2695-10 μM | F2695-100 μM | F2696-1 μM | F2696-10 μM | F2696-100 μM | C 218-1 μM | C 218-10 μM | C 218-100 μM | |
|---|---|---|---|---|---|---|---|---|---|---|---|---|
| Up | >1.7 | Up | | | | | | 10 | 1 | 1 | 4 | |
| Down | <0.588 | Down | | | | | 5 | 6 | 7 | 12 | 12 | |
| | | TI | | | | | 5 | 16 | 8 | 13 | 16 | |
| Pos | No. U | No. D | | | | | | | | | | Gene |
| A09 | 3 | | | | | | | | 2.90 | 2.23 | 2.14 | *H. sapiens* mitochondrion, 12S |
| B20 | | 2 | | | | | | | | 0.14 | 0.27 | *H. sapiens* chromosome 19, BAC CIT-B-191n6 |
| B22 | | 2 | | | | | | | | 0.17 | 0.32 | *H. sapiens* Genomic sequence from 17 |
| C01 | 1 | | | | | | | 3.20 | | | | *H. sapiens* mitochondrion, 16S |
| E05 | | 2 | | | | | | | | 0.22 | 0.35 | *H. sapiens* DNA sequence from clone 740A11 on chromosome Xq22.2–23. Contains part of the COL4A5 gene for Collagen Alpha 5 (IV) Chain Precursor. Contains GSS1, complete sequence |
| E11 | 1 | | | | | | | 2.12 | | | | *H. sapiens* chlordecone reductase homolog liver, mRNA |
| G01 | 1 | | | | | | | | | | 2.04 | *H. sapiens* estrogen receptor-related protein (variant ER from breast cancer) mRNA |
| G05 | 1 | | | | | | | | | | 2.02 | *H. sapiens* mitochondrion, cytochrome c oxidase subunit 1 |
| G09 | 1 | | | | | | | 2.09 | | | | *H. sapiens* mitochondrion, cytochrome b |
| I01 | 1 | | | | | | | 2.05 | | | | *H. sapiens* mitochondrion, cytochrome c oxidase subunit 1 |
| I18 | 1 | | | | | | | 2.38 | | | | *H. sapiens* 18S rRNA gene |
| J03 | 1 | | | | | | | 2.12 | | | | *H. sapiens* CLP mRNA |
| L01 | 1 | | | | | | | 2.05 | | | | *H. sapiens* divalent cation tolerant protein CUTA mRNA |
| M07 | 1 | | | | | | | 2.25 | | | | *H. sapiens* mitochondrion, cytochrome c oxidase subunit 1 |
| M12 | | 3 | | | | | | 0.21 | | 0.16 | 0.39 | *H. sapiens* mRNA; cDNA DKFZp564C1563 |
| S01 | 1 | | | | | | | | | | 2.98 | *Mus muculus* TCR beta locus |
| T08 | | 5 | | | | | 0.22 | 0.20 | 0.35 | 0.14 | 0.22 | *H. sapiens* mRNA for KIAA1185 protein |
| U04 | | 5 | | | | | 0.26 | 0.19 | 0.48 | 0.22 | 0.37 | *H. sapiens* translation initiation factor eIF-2alpha mRNA |
| W17 | 1 | | | | | | | 2.96 | | | | *H. sapiens* mitochondrion, hypoxia inducible gene-14 |
| X02 | | 5 | | | | | 0.29 | 0.20 | 0.36 | 0.24 | 0.31 | unk |
| X05 | | 2 | | | | | | | | 0.15 | 0.24 | *H. sapiens* microsomal epoxide hydrolase (EPHX) gene |
| X06 | | 5 | | | | | 0.20 | 0.16 | 0.23 | 0.15 | 0.23 | *H. sapiens* Genomic sequence from 9q34 |
| Y17 | 1 | | | | | | | 2.65 | | | | *H. sapiens* 28S ribosomal RNA gene |
| Z13 | | 3 | | | | | | | 0.34 | 0.29 | 0.27 | unk |
| AA11 | | 3 | | | | | | | 0.38 | 0.27 | 0.31 | *H. sapiens* Repeat sequence AluJb fragment inserted into a cDNA coding for an unknown protein |
| AC13 | | 5 | | | | | 0.22 | 0.16 | 0.28 | 0.16 | 0.28 | *H. sapiens* 7S RNA gene |

The following Toxicity Indices were obtained:

| F2695 | Toxicity Index |
|---|---|
| 1 µM | 0 |
| 10 µM | 0 |
| 100 µM | 0 |

| C218 | Toxicity Index |
|---|---|
| 1 µM | 8 |
| 10 µM | 13 |
| 50 µM | 16 |

| F2696 | Toxicity Index |
|---|---|
| 1 µM | 0 |
| 10 µM | 5 |
| 100 µM | 16 |

According to these parameters, the following ranking could be put forward, from the most toxic to the least toxic: C218 (clomipramine)>F2696>>>>>F2695.

With regard to over- and under-expressed clones at a Factor of 2, F2695 did not induce any signatures, even at a concentration of 100 µM.

The concentration effect on the occurrence of signatures was confirmed by the fact that the weak signatures with F2696 at 1 µM, which were present in the preceding analysis with an Induction factor of 1.7, disappear.

From a qualitative standpoint, the impact of F2696 and of clomipramine on Cox1 and on cytochrome b was also confirmed (G05/G09/I01 positions).

F2695, the pharmacologically-active enantiomer of F2207, was without significant impact in this test, whereas clomipramine is used as positive-control reference product.

Conversely, F2696, the pharmacologically-inactive enantiomer of F2207, showed a profile of signatures that is quantitatively and qualitatively close to that of clomipramine, and shows no signatures in common with F2695.

All of this is evidence of a superior toxico-genomic profile for the active F2695 enantiomer which, in this experimental model, had a very significantly better safety coefficient than that of F2696.

4.4 Conclusion

The genomic pharmacotoxicology studies performed on the F2695 and F2696 molecules, enantiomers of F2207 (at concentrations of 10, 50 and 100 µM), and on C218 (clomipramine, at concentrations of 1, 10 and 50 µM), using rat hepatocytes in primary culture, yielded concentration-dependent stress signatures and Toxicity Indices. These studies confirm the capacity of the genomic pharmacotoxicology test to reveal stress signatures under treatment conditions (concentrations, duration of treatment) that do not cause any toxicity in a classic cell-viability assay such as the MTT assay.

This study brings to light several important facts:

in the primary rat hepatocyte model, only F2695, the pharmacologically-active enantiomer of F2207, did not induce a significant Toxicity Index;

F2696, the inactive enantiomer of F2207, and clomipramine, the reference psychotropic product, induced marked Indices involving very similar or common stress signatures. In this system, clomipramine, the positive-control reference molecule, induced the highest number of stress signatures, significant indices having been observed starting at the lowest concentrations. On this subject, it is interesting to note that clomipramine can induce a certain number of adverse events in man, such as tachycardia, orthostatic hypotension, cardiac conduction or rhythm disturbances, and exceptionally hepatitis. In cases of accidental overdosage with clomipramine, syncope, hematological disturbances and severe cardiovascular manifestations can be observed.

Without inferring a common physiopathological mechanism, it is interesting to note that F2696 showed very similar or common stress signatures to those of clomipramine and also induces adverse events such as the cardiovascular disturbances previously described.

Thus, it is legitimate to suggest that the signatures observed are independent of any antidepressant, or more broadly psychotropic, profile. On the contrary, the signatures should indeed be considered to be "signatures of stress" (F2696 causes in particular reduced expression of a gene involved in protein synthesis and of a translation initiation factor). All of this is evidence of a superior toxico-genomic profile for the active F2695 enantiomer which, in this experimental model, had a very significantly better safety coefficient than that of F2696.

The invention claimed is:

1. A method for limiting the risk of cardiovascular disturbances and/or the risks of organ and/or tissue toxicity in the treatment of a living animal body afflicted with disorders which may be treated by double inhibition of serotonin (5-HT) and norepinephrine (NE) reuptake, said method comprising administering to the living animal body an effective amount of a mixture of enantiomers of milnacipran (Z(±)-2-(amino methyl)-N,N-diethyl-1-phenylcyclopropanecarboxamide), as well as their pharmaceutically-acceptable salts, other than the hydrochloride salt, such mixture being substantially pure in the (1S,2R) enantiomer, wherein the administration of said mixture limits the risks of cardiovascular disturbances and/or the risks of organ and/or tissue toxicity, relative to administration of racemic milnacipran.

2. The method of claim 1, wherein the cardiovascular disturbance corresponds to an increase in blood pressure and/or an increase in heart rate.

3. The method of claim 2, wherein the increase in blood pressure corresponds to an increase in diastolic blood pressure.

4. The method according to claim 1, wherein the organ toxicity is cardiac toxicity and the tissue toxicity is hepatic and/or renal toxicity.

5. The method according to claim 1, wherein mass/mass ratio between the (1S,2R) enantiomer and (1R,2S) enantiomer in the mixture is greater than 95:5 ((1S,2R):(1R,2S)).

6. The method according to claim 1, wherein mass/mass ratio between the (1S,2R) enantiomer and (1R,2S) enantiomer in the mixture is greater than 99:1 ((1S,2R):(1R,2S)).

7. The method according to claim 1, wherein mass/mass ratio between the (1S,2R) enantiomer and (1R,2S) enantiomer in the mixture is greater than 99.5:0.5 ((1S,2R):(1R, 2S)).

8. The method according to claim 1, wherein the disorder or condition is selected from depression, bi-polar disease, schizophrenia, generalised anxiety, morose and marasmic states, stress-related diseases, panic attacks, phobias, obsessive-compulsive disorders, behavioural disorders, oppositional disorders, post-traumatic stress disorder, depression of the immune system, fatigue and the associated pain syndromes, chronic fatigue syndrome, fibromyalgia, and other functional somatic disorders, autism, disorders characterised by attention deficit due to general health status, attention disorders due to hyperactivity, eating disorders, neurotic bulimia, neurotic anorexia, obesity, psychotic disorders, apathy, migraine, pain, irritable bowel syndrome, cardiovascular diseases, neuro-degenerative diseases and the associated anxiety-depressive syndromes (Alzheimer's disease, Huntington's chorea, Parkinson's disease), urinary incontinence, drug addiction.

9. The method of claim 8, wherein depression is selected from deep depression, resistant depression, depression in the elderly, psychotic depression, depression induced by treatments with interferon, depressive state, manic-depressive syndrome, seasonal depressive episodes, depressive episodes related to general health status, depression rotated to mood-altering substances.

10. The method of claim 8, wherein the phobia is agoraphobia.

11. The method of claim 8, wherein the pain is chronic pain.

12. The method of claim 8, wherein the cardiovascular disease is selected from anxiety-depressive syndrome in myocardial infarct or in hypertension.

13. The method of claim 8, wherein the urinary incontinence is selected from urinary incontinence related to stress and enuresis.

14. The method of claim 8, wherein the drug addiction is selected from anxiety addiction to tobacco, to nicotine, to alcohol, to narcotics, to drugs, and to an analgesic used in weaning-off from these addictive states.

15. The method according to claim 1, wherein the living animal body is selected from children, the elderly, patients with hepatic and/or renal insufficiency, patients receiving treatment that induces hepatic or renal organ and/or tissue toxicity, patients receiving treatment for a heart condition, patients receiving treatment that induces cardiovascular side-effects, and patients having a history of cardiovascular disease and/or suffering from cardiovascular disorders.

16. The method according to claim 15, wherein the history of cardiovascular disease and/or cardiovascular disorders are chosen among myocardial infarct, cardiac rhythm disorders (tachycardia, bradycardia, palpitations), blood pressure disorders (hypo- or hypertensive patients) and heart disease.

17. A method for limiting the risks of cardiovascular disturbances and/or the risks of organ and/or tissue toxicity in the treatment of a living animal body afflicted with depression, which comprises administering to the living animal body:

a) a mixture of enantiomers substantially pure in the (1S,2R) enantiomer of milnacipran as well as their pharmaceutically-acceptable salts, other than the hydrochloride salt, wherein the administration of said mixture limits the risks of cardiovascular disturbances and/or the risks of organ and/or tissue toxicity, relative to administration of racemic milnacipran, and b) at least one active compound selected from the psychotropic, in particular antidepressants, and antimuscarinic agents, as associated products for use simultaneously, separately or staggered in time.

18. The method according to claim 17, wherein the depression is selected from deep depression, resistant depression, depression in the elderly, psychotic depression, depression induced by treatment with interferon, depressive state, manic-depressive syndrome, seasonal depressive episodes, depressive episodes related to general health status, depressive episodes related to mood-altering substances.

19. A method for limiting the risks of organ and/or tissue toxicity in the treatment of a living animal body afflicted with conditions or disorders which may be treated by double inhibition of serotonin (5-HT) and norepinephrine (NE) reuptake, which comprises administering to the living animal body:

a) a mixture of enantiomers substantially pure in the (1S,2R) enantiomer of milnacipran as well as their pharmaceutically-acceptable salts, other than the hydrochloride salt, wherein the administration of said mixture limits the risks of cardiovascular disturbances and/or the risks of organ and/or tissue toxicity, relative to administration of racemic milnacipran, and b) at least one other active substance selected from the active compounds tat induce organ toxicity and the active compounds that induce cell toxicity, in particular hepatic and/or renal, as associated products for use simultaneously, separately or staggered in time.

20. A method for limiting the risks of cardiovascular disturbances in the treatment of a living animal body afflicted with conditions or disorders which may be treated by double inhibition of serotonin (5-HT) and norepinephrine (NE) reuptake, which comprises administering to the living animal body:

a) a mixture of enantiomers substantially pure in the (1S,2R) enantiomer of milnacipran as well as their pharmaceutically-acceptable salts, other than the hydrochloride salt, wherein the administration of said mixture limits the risks of cardiovascular disturbances and/or the risks of organ and/or tissue toxicity, relative to administration of racemic milnacipran, and b) at least one other active substance selected from the active compounds that induce cardiovascular side-effects, as associated products for use simultaneously, separately or staggered in time.

21. A method for treating conditions or disorders by double inhibition of serotonin (5-HT) and norepinephrine (NE) reuptake in a living animal body, while limiting the risks of cardiovascular disturbances and/or the risks of organ and/or tissue toxicity, which comprises administering to the living animal body an effective amount of a mixture of enantiomers of milnacipran (Z(±)-2-(amino methyl)-N,N-diethyl-1-phenylcyclopropanecarboxamide) as well as their pharmaceutically-acceptable salts, other than the hydrochloride salt, such mixture being substantially pure in the (1S, 2R) enantiomer wherein the administration of said mixture limits the risks of cardiovascular disturbances and/or the risks of organ and/or tissue toxicity, relative to administration of racemic milnacipran.

22. The method of claim 21, wherein the cardiovascular disturbance corresponds to an increase in blood pressure and/or an increase in heart rate.

23. The method of claim 22, wherein the increase in blood pressure corresponds to an increase in diastolic blood pressure.

24. The method of claim 21, wherein the organ toxicity is cardiac toxicity and the tissue toxicity is hepatic and/or renal toxicity.

25. The method of claim 21, wherein mass/mass ratio between the (1S,2R) enantiomer and (1R,2S) enantiomer in the mixture is greater than 95:5 ((1S,2R):(1R,2S)).

26. The method of claim 21, wherein mass/mass ratio between the (1S,2R) enantiomer and (1R,2S) enantiomer in the mixture is greater than 99:1 ((1S,2R):(1R,2S)).

27. The method of claim 21, wherein mass/mass ratio between the (1S,2R) enantiomer and (1R,2S) enantiomer in the mixture is greater than 99.5:0.5 ((1S,2R):(1R,2S)).

28. The method of claim 21, wherein the disorder or condition is selected from depression, bi-polar disease, schizophrenia, generalised anxiety, morose and marasmic states, stress-related diseases, panic attacks, phobias, obsessive-compulsive disorders, behavioural disorders, oppositional disorders, post-traumatic stress disorder, depression of the immune system, fatigue and the associated pain syndromes, chronic fatigue syndrome, fibromyalgia, and other functional somatic disorders, autism, disorders characterised by attention deficit due to general health status, attention disorders due to hyperactivity, eating disorders, neurotic bulimia, neurotic anorexia, obesity, psychotic disorders, apathy, migraine, pain, irritable bowel syndrome, cardiovascular diseases, neuro-degenerative diseases and the associated anxiety-depressive syndromes (Alzheimer's disease, Huntington's chorea, Parkinson's disease), urinary incontinence, drug addiction.

29. The method of claim 28, wherein depression is selected from deep depression, resistant depression, depression in the elderly, psychotic depression, depression induced by treatments with interferon, depressive state, manic-depressive syndrome, seasonal depressive episodes, depressive episodes related to general health status, depression related to mood-altering substances.

30. The method of claim 28, wherein the phobia is agoraphobia.

31. The method of claim 28, wherein the pain is chronic pain.

32. The method of claim 28, wherein the cardiovascular disease is selected from anxiety-depressive syndrome in myocardial infarct or in hypertension.

33. The method of claim 28, wherein the urinary incontinence is selected from urinary incontinence related to stress and enuresis.

34. The method of claim 28, wherein the drug addiction is selected from anxiety addiction to tobacco, to nicotine, to alcohol, to narcotics, to drugs, and to an analgesic used in weaning-off from these addictive states.

35. The method of claim 21, wherein the living animal body is selected from children, the elderly, patients with hepatic and/or renal insufficiency, patients receiving treatment that induces hepatic or renal organ and/or tissue toxicity, patients receiving treatment for a heart condition, patients receiving treatment that induces cardiovascular side-effects, patients having a history of cardiovascular disease and/or suffering from cardiovascular disorders.

36. The method of claim 35, wherein the history of cardiovascular disease and/or cardiovascular disorders are chosen among myocardial infarct, cardiac rhythm disorders (tachycardia, bradycardia, palpitations), blood pressure disorders (hypo- or hypertensive patients) and heart disease.

37. A method for treating depression in a living animal body, while limiting the risks of cardiovascular disturbances and/or the risks of organ and/or tissue toxicity which comprises administering to said living animal body:

a) a mixture of enantiomers substantially pure in the (1S,2R) enantiomer of milnacipran as well as their pharmaceutically-acceptable salts, other than the hydrochloride salt, wherein the administration of said mixture limits the risks of cardiovascular disturbances and/or the risks of organ and/or tissue toxicity, relative to administration of racemic milnacipran, and b) at least one active compound selected from the psychotropics, in particular antidepressants, and antimuscarinic agents, as associated products for use simultaneously, separately or staggered in time.

38. The method according to claim 37, wherein the depression is selected from deep depression, resistant depression, depression in the elderly, psychotic depression, depression induced by the treatment with interferon, depressive state, manic-depressive syndrome, seasonal depressive episodes, depressive episodes related to general health status, depressive episodes related to mood-altering substances.

39. A method for treating conditions or disorders by double inhibition of serotonin (5-HT) and norepinephrine (NE) reuptake, in a living animal body, while limiting the risks of organ and/or tissue toxicity which comprises administering to said living animal body:

a) a mixture of enantiomers substantially pure in the (1S,2R) enantiomer of milnacipran as well as their pharmaceutically-acceptable salts, other than the hydrochloride salt, wherein the administration of said mixture limits the risks of cardiovascular disturbances and/or the risks of organ and/or tissue toxicity, relative to administration of racemic milnacipran, and b) at least one other active substance selected from the active compounds that induce organ toxicity and the active compounds that induce cell toxicity, in particular hepatic and/or renal, as associated products for use simultaneously, separately or staggered in time.

40. A method for treating conditions or disorders by double inhibition of serotonin (5-HT) and norepinephrine (NE) reuptake, in a living animal body, while limiting the risk of cardiovascular disturbances which comprises administering to said living animal body:

a) a mixture of enantiomers substantially pure in the (1S,2R) enantiomer of milnacipran as well as their pharmaceutically-acceptable salts, other than the hydrochloride salt, wherein the administration of said mixture limits the risks of cardiovascular disturbances and/or the risks of organ and/or tissue toxicity, relative to administration of racemic milnacipran, and b) at least one other active substance selected from the active compounds that induce cardiovascular side-effects, as associated products for use simultaneously, separately or staggered in time.

* * * * *

UNITED STATES PATENT AND TRADEMARK OFFICE
CERTIFICATE OF CORRECTION

| | |
|---|---|
| PATENT NO. | : 7,074,833 B2 |
| APPLICATION NO. | : 10/805940 |
| DATED | : July 11, 2006 |
| INVENTOR(S) | : Jean Deregnaucourt et al. |

It is certified that error appears in the above-identified patent and that said Letters Patent is hereby corrected as shown below:

On Title Page, Item (73) Col. 1
Assignee Information:   "Boulogne-Billancourt" should be -- Castres --.

Column 38, Line 29:        "tat" should be -- that --.

Signed and Sealed this

Nineteenth Day of September, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,074,833 B2 |
| APPLICATION NO. | : 10/805940 |
| DATED | : July 11, 2006 |
| INVENTOR(S) | : Jean Dereganaucourt et al. |

It is certified that error appears in the above-identified patent and that said Letters Patent is hereby corrected as shown below:

Column 37, Line 27:   "rotated" should be -- related --.

Column 39, Line 40:   "wherein the phobia" should be -- wherein phobia --.

Signed and Sealed this

Fifteenth Day of July, 2008

JON W. DUDAS
*Director of the United States Patent and Trademark Office*